United States Patent [19]

Roehrig et al.

[11] Patent Number: 6,075,879
[45] Date of Patent: Jun. 13, 2000

[54] METHOD AND SYSTEM FOR COMPUTER-AIDED LESION DETECTION USING INFORMATION FROM MULTIPLE IMAGES

[75] Inventors: Jimmy R. Roehrig, Palo Alto; Alexander C. Schneider, Mountain View; Shih-Ping Wang, Los Altos, all of Calif.

[73] Assignee: R2 Technology, Inc., Los Altos, Calif.

[21] Appl. No.: 09/178,901

[22] Filed: Oct. 26, 1998

Related U.S. Application Data

[63] Continuation-in-part of application No. 08/980,254, Nov. 28, 1997, and a continuation-in-part of application No. 08/579,802, Dec. 28, 1995, Pat. No. 5,828,774, and a continuation-in-part of application No. 08/438,432, May 10, 1995, Pat. No. 5,729,620, and a continuation-in-part of application No. 08/129,255, Sep. 29, 1993, abandoned.

[51] Int. Cl.$^7$ ..................................................... G06K 9/00
[52] U.S. Cl. ............................. 382/132; 378/37; 128/922
[58] Field of Search .................................... 382/128, 131, 382/132, 284, 173, 224; 378/37; 128/920, 922

[56] References Cited

U.S. PATENT DOCUMENTS

| | | | |
|---|---|---|---|
| 5,452,367 | 9/1995 | Bick et al. | 382/128 |
| 5,491,627 | 2/1996 | Zhang et al. | 128/664 |
| 5,537,485 | 7/1996 | Nishikawa et al. | 382/132 |
| 5,572,565 | 11/1996 | Abdel-Mottaleb | 378/37 |
| 5,579,360 | 11/1996 | Abdel-Mottaleb | 378/37 |
| 5,657,362 | 8/1997 | Giger et al. . | |
| 5,815,591 | 9/1998 | Roehrig et al. | 382/130 |
| 5,941,832 | 8/1999 | Tumey et al. | 600/549 |
| 5,982,917 | 11/1999 | Clarke et al. | 382/132 |
| 5,999,639 | 12/1999 | Rogers et al. | 382/132 |

OTHER PUBLICATIONS

Baker et al., 1996, "Artificial Neural Network: Improving the Quality of Breast Biopsy Recommendations," *Radiology* 198:131–135.

Bick et al., 1995, "A New Single–Image Method for Computer–Aided Detection of Small Mammographic Masses, "In: *Computer Assisted Radiology: Proceedings of the International Symposium on Computer and Communication Systems for Image Guided Diagnosis and Therapy*, Lemke et al., eds. CAR'95 Berlin, Jun. 21–24, 1995.

Doi et al., 1995, "Potential Usefulness of Digital Imaging in Clinical Diagnostic Radiology: Computer Aided Diagnosis," *Journal of Digital Imaging* 8(1):2–7.

(List continued on next page.)

*Primary Examiner*—Bhavesh Mehta
*Attorney, Agent, or Firm*—Pennie & Edmonds LLP

[57] ABSTRACT

A system, method, and computer program product for computer-aided detection of suspicious lesions in digital mammograms is described, wherein single-view feature vectors from a first digital mammogram are processed in a classification algorithm along with information computed from a plurality of related digital mammograms to assign an overall probability of suspiciousness to potentially suspicious lesions in the first digital mammogram. In one preferred embodiment, a greater probability of suspiciousness is determined where there are similar corresponding lesions in the first digital mammogram and in an alternate digital mammogram view of the same breast. In another preferred embodiment, a lesser probability of suspiciousness is found where there are symmetric lesions or structures located in the first digital mammogram and a digital mammogram of the opposite breast. In another preferred embodiment, a lesser probability of suspiciousness is found where there are similar lesions or structures located in the first digital mammogram and a digital mammogram of the same breast taken months or years earlier in time. In another preferred embodiment, the nipple location, which serves as a reference location point across different digital mammogram, is located using an algorithm that takes into account the chest wall, the skin line of the breast, and the general orientation of the fibrous breast tissue in the digital mammogram relative to the chest wall.

47 Claims, 11 Drawing Sheets

OTHER PUBLICATIONS

Feig and Yaffe, 1995, "Digital Mammography, Computer–Aided Diagnosis, and Telemammography," *The Radiologic Clinics of North America: Breast Imaging* *33*(6):1205–1230.

Floyd et al., 1994, "Prediction of Breast Cancer Malignancy Using an Artificial Neural Network," *Cancer* *74*(11):2944–2948.

Frankel et al., 1995 "Initial Versus Subsequent Screening Mammography: Comparison of Findings and Their Prognostic Significance," *AJR:164*: 1107–1109.

Giger et al., 1993, "An 'Intelligent' Workstation for Computer–aided Diagnosis," *Radiographics* *13*(3):647–656.

Gurney, 1994, "Neural Networks at the Crossroads: Caution Ahead," *Radiology* *193*:27–30.

Ikeda and Sickles, 1988, "Second–screening Mammography: One versus Two Views per Breast," *Radiology* *168*: 651–656.

Karssemeijer, 1994, "Recognition of stellate lesions in digital mammograms,"In :*Digital Mammography*, Gale et al., eds., pp. 211–219.

Karssemeijer, 1995, "Detection of stellat distortions in mammograms using scale space operators," *In : Information Processing in Medical Imaging*, Biszais et al., Kluwer Academic Publishers, Netherlands, pp. 335–346.

Katsuragawa, 1990, "Image feature analysis and computer–aided diagnosis in digital radiography: Effect of digital parameters on the accuracy of computerized analysis of interstitial disease in digital chest radiographs," *Med. Phys.* *17*(1):72–78.

Kegelmeyer et al., 1994, "Computer–aided Mammographic Screening for Spriculated Lesions," *Radiology* *1991*:331–337.

Lin et al., "Application of Neural Networks for Improvement of Lung Nodule Detection in Digital Chest Radiographs," pp. IV–20–IV–23.

Matsubara et al., "Development of a New Algorithm For Detection of Mammographic Masses".

Miller and Astley, 1993, "Automated Detection of Mammographic Asymmetry Using Anatomical Features," *International Journal of Pattern Recognition and Artificial Intelligence* *7* (6): 1461–1476.

Miller and Astley, 1993, "Detection of breast asymmetry using anatomical features," *SPIE* *1905*:433–442.

Nishikawa et al., "Computer–aided Detection and Diagnosis of Masses and Clustered Microcalcifications from Digital Mammograms," In: *State of the Art in Digital Mammographic Image Analysis*, Bowyer and Astley, eds. World Scientific Publishing Co., 1993.

Schmidt et al., "Computer–aided Diagnosis in Mammography," *RSNA Categorical Course in Breast Imaging 1995*; pp. 199–208.

Specht, 1990, "Probabilistic Neural Networks," *Neural Networks* *3*:109–118.

Sprecht, "Enhancements to Probabilistic Neural Networks," Proceedings of the IEEE International Joint Conference on Neural Networks, Baltimore, MD. Jun. 7–11, 1992.

Sprecht and Romsdahl, "Experience with Adaptive Probabilistic Neural networks and Adaptive General Regression Neural Networks," IEEE International Conference on Neural Networks, Orlando, Florida. Jun. 28 to Jul. 1994.

Tahoces et al., 1995, "Computer–assisted diagnosis: the classification of mammographic breast parenchymal patterns," *Phys. Med. Biol.* *40*:103–117.

te Brake and Karssemeijer, 1996, "Detection of Stellate Breast Abnormalities," In: *Digital Mammography '96*, Doi et al., eds. Elsevier Science B. V. pp. 341–346.

Thurfjell et al., 1988, "Sensitivity and Specificity of Computer–Assisted Breast Cancer Detection in Mammongraphy Screening," *Acta Radiologica* *39*:384–388.

Wei et al., 1995, "Classification of mass and normal breast tissue on digital mammograms: Multiresolution texture analysis," *Med. Phys.* *22*:(9):1501–1513.

Wu et al., 1993, "Artificial Neural Networks in Mammography: Application to Decision Making in the Diagnosis of Breast Cancer," *Radiology* *187*:81–87.

Yin et al., 1993, "Comparison of Bilateral–Subtraction and Single–Image Processing Techniques in the Computerized Detection of Mammographic Masses," *Investigative Radiology* *28*:473–481.

Yin et al., 1991, "Computerized detection of masses in digital mammograms: Analysis of bilateral subtraction images," *Med. Phys.* *18*(5):955–963.

Yoshimura et al., 1992, "Computerized Scheme for the Detection of Pulmonary Nodules: A Nonlinear Filtering Technique," *Invest. Radiol.* *27*:124–129.

Zhang and Giger, 1995, "Automated detection of spiculated lesions and architectural distortions of digitized mammograms," *SPIE* *2434*:846–854.

METHOD AND SYSTEM FOR COMPUTER-AIDED LESION DETECTION USING INFORMATION FROM MULTIPLE IMAGES

REFERENCE TO RELATED APPLICATIONS

This application is a continuation-in-part of copending parent application Ser. No. 08/980,254, filed on Nov. 28, 1997. In turn, Ser. No. 08/980,254 is a continuation-in-part of parent applications Ser. No. 08/579,802 filed on Dec. 28, 1995 (now U.S. Pat. No. 5,828,774) and Ser. No. 08/438,432 filed on May 10, 1995 (now U.S. Pat. No. 5,729,620). In turn, Ser. No. 08/579,802 is a continuation, and Ser. No. 08/438,432 is a continuation-in-part, of parent application Ser. No. 08/129,255, filed Sep. 29, 1993 (abandoned). This application hereby incorporates by reference each of said parent applications into the present disclosure.

FIELD OF THE INVENTION

The present invention relates to the field of computer aided diagnosis of medical images. In particular, the invention relates to a method and apparatus for computer-aided lesion detection using information from multiple digital mammogram images for allowing more sensitive and reliable identification of suspicious, i.e., possibly cancerous, lesions.

BACKGROUND OF THE INVENTION

Systems for computer-aided diagnosis ("CAD") assist radiologists in the detection and classification of abnormal lesions in medical images. The purpose of such devices, as described in U.S. Pat. No. 5,815,591 to Roehrig, et. al., entitled "Method and Apparatus for Fast Detection of Spiculated Lesions in Digital Mammograms," the disclosure of which is hereby incorporated by reference in the present application, is to direct the attention of a radiologist to suspicious areas of the medical image that may reflect a threatening condition. While not a replacement for the experienced radiologist, CAD systems are designed to increase efficiency and reduce error, as a typical radiologist may be required to examine hundreds of medical images per day, which can lead to the possibility of a missed diagnosis due to human error.

Desired characteristics of a CAD system for analyzing mammograms include higher sensitivity, i.e., the ability to detect more subtle indications of abnormalities, coupled with lower false positive rates, i.e., the number of areas marked "suspicious" by the CAD system which, in reality, are not suspicious or indicative of a possibly cancerous condition. Generally speaking, it is desirable to minimize both the rate of false negatives, also called "misses", as well as the rate of false positives.

Today, conventional CAD systems usually treat each digital mammogram separately. In these systems, the plurality of mammograms that are usually taken of a woman's breasts—for example, the craniocaudal ("CC") and mediolateral oblique ("MLO") views of each of the left and right breasts, respectively—are digitized into digital mammograms and processed separately by the CAD system for detecting suspicious lesions. Suspicious lesions are located on each of the four images separately, without regard for what regions are found or not found in the other images. Although "mammogram" is sometimes used in the art to depict a set of four related films or views but sometimes used to depict one such view, for clarity purposes, the term "mammogram" shall correspond to a one of the related films or views taken during the mammography process.

However, in radiology practice it has been found that if the same abnormality appears in two different views of the same breast, then that abnormality has a higher probability of being a true lesion. This is because normal overlying tissue structures may accidentally appear to be an abnormal lesion in a single digital mammogram, tissue structures which will appear different or nonexistent in a different view. Accordingly, there is a lower probability of false positives when two different views of the same breast are examined, due to the lower probability of false or accidental crossing of tissue structure in the same region on two separate views of one breast.

Additionally, in radiology practice it has been found that if similar potentially suspicious structures are found in both the left and right breast, then those structures have a lower probability of being true lesions. Likewise, if a potentially suspicious structure is found in one breast but no corresponding structure is found in the opposite breast, there is a higher probability that the structure represents a true lesion. This is because normal tissue structure is usually similar between left and right breasts.

Moreover, if a breast develops a potentially suspicious lesion over a period of time as reflected by periodic mammograms of that breast, the likelihood increases that it is a true lesion. Accordingly, it is often useful to compare similar mammogram views of the same breast taken at different times, typically twelve months apart.

In comparing multiple views of a single breast or opposing breasts, it is necessary to have a common reference from which to measure the location of potentially suspicious lesions in each view. One such reference point is the nipple of the breast. A problem arises, however, in that the breast is often manipulated during the mammography process in various ways, such that the nipple may be in different and sometimes unpredictable locations in the digital mammogram. The nipple may, or may not, correspond to the location along the skin line furthest from the chest wall.

In "Computerized detection of masses in digital mammograms: Analysis of bilateral subtraction images," Med. Phys. 18 (5), September/October 1991, Yin and Giger et. al. disclose a bi-lateral subtraction technique, in which one image is rotated and translated to best match the other image, and then left and right images are subtracted from each other pixel-by-pixel. The resulting difference image is then thresholded to obtain several "starting points" which represent the areas of largest difference between left and right breasts. However, in the Yin and Giger et. al. disclosure, it is only raw pixels that are compared between left and right breasts, and the simple output obtained is only a starting point for further analysis.

In U.S. Pat. No. 5,579,360, Abdel-Mottaleb describes mass detection by computer using digital mammograms of the same breast taken from different viewing directions. Abdel-Mottaleb describes a method in which position, size, shape, intensity variance, and brightness are each directly compared between the two views of the same breast. The disclosed Abdel-Mottaleb method is disadvantageous, however, in that if any one such measure between views does not correlate within specified boundaries, the suspect spot is marked as a false positive, whereas correlated spots meeting all criteria lead directly to a mark on the output display directing the attention of the radiologist to that spot. Such a binary approach can often accord inordinate weight to the inter-view comparison process, at the expense of strong indicators that may still exist within a single view.

Accordingly, it would be desirable to provide a computer-aided diagnosis system that uses information from multiple digital mammograms to provide sensitive, fast, and reliable identification of suspicious, lesions in a digital mammogram.

It would be further desirable to provide a computer-aided diagnosis system that processes information from a first digital mammogram view of a breast, together with comparative information from a plurality of views of the same breast, to arrive at an overall suspiciousness determination regarding potentially suspicious lesions in the first digital mammogram view.

It would be further desirable to provide a computer-aided diagnosis system capable of locating the nipple in a digital mammogram in a reliable manner that accommodates different nipple locations corresponding to different breast manipulations that may take place during the mammography process.

It would be further desirable to provide a computer-aided diagnosis system that processes information from a first digital mammogram view of a breast, together with comparative information from a digital mammogram of the opposite breast, to arrive at an overall suspiciousness determination regarding potentially suspicious lesions in the first digital mammogram view.

It would be even further desirable to provide a computer-aided diagnosis system that processes information from a first digital mammogram view of a breast, together with comparative information from a digital mammogram of the same breast taken earlier in time, to arrive at an overall suspiciousness determination regarding potentially suspicious lesions in the first digital mammogram view.

It would be still further desirable to provide a computer-aided diagnosis system that processes information from a first digital mammogram view of a breast, together with comparative information from (a) a different digital mammogram view of the same breast, (b) a digital mammogram of the opposite breast, and (c) a digital mammogram of the same breast taken earlier in time, to arrive at an overall suspiciousness determination regarding potentially suspicious lesions in the first digital mammogram view.

SUMMARY OF THE INVENTION

These and other features are provided in a system, method, and computer program product for computer-aided detection of suspicious lesions in digital mammograms, wherein single-view feature vectors from a first digital mammogram are processed in a classification algorithm along with information computed from a plurality of related digital mammograms to assign an overall probability of suspiciousness to potentially suspicious lesions in the first digital mammogram. In a preferred embodiment, a first digital mammogram and a second digital mammogram taken from a different view of the same are processed, with single-view feature vectors corresponding to potentially suspicious lesions being separately computed for each digital mammogram and then compared to produce similarity metrics. If a potentially suspicious lesion in the first digital mammogram has a high degree of similarity with a potentially suspicious lesion in the second digital mammogram, there is a greater probability that the potentially suspicious lesion is a true lesion.

In another preferred embodiment, a first digital mammogram and a second digital mammogram taken from opposite breasts are processed, with single-view feature vectors of potentially suspicious lesions being separately computed for each digital mammogram and then compared to produce symmetry metrics. If a potentially suspicious lesion in the first digital mammogram has a high degree of similarity with a potentially suspicious lesion in the second digital mammogram, there is a lesser probability that the potentially suspicious lesion is a true lesion.

In another preferred embodiment, a lesser probability of suspiciousness is found where there are similar lesions or structures located in the first digital mammogram and a digital mammogram of the same breast taken months or years earlier in time. In still another preferred embodiment, single-view feature vectors from a first digital mammogram are classified in conjunction with information from each of (a) symmetry metrics computed in relation to a digital mammogram of the opposite breast, (b) similarity metrics computed in relation to a digital mammogram of the same breast taken from a different view, and (c) similarity metrics computed in relation to the same breast taken at a prior time. Symmetry and similarity metrics taken from related views are not used as hard limiters directly coupled to the output display, but rather serve as useful data to influence the probabilistic outcome of a single-view classification scheme in accordance with a preferred embodiment.

In another preferred embodiment, the nipple location is determined using an algorithm that takes into account the chest wall, the skin line of the breast, and the general orientation of the fibrous breast tissue in the digital mammogram relative to the chest wall. The nipple location is determined by segmenting the digital mammogram for determining the position of the chest wall of the breast, determining a most prominent direction of lines in the breast tissue relative to the chest wall for the digital mammogram, segmenting the digital mammogram for determining the location of the skin line of the breast, and selecting the location of the nipple as the furthest point along the skin line from the chest wall as measured along the most prominent direction of lines.

DETAILED DESCRIPTION

Figure 1A:
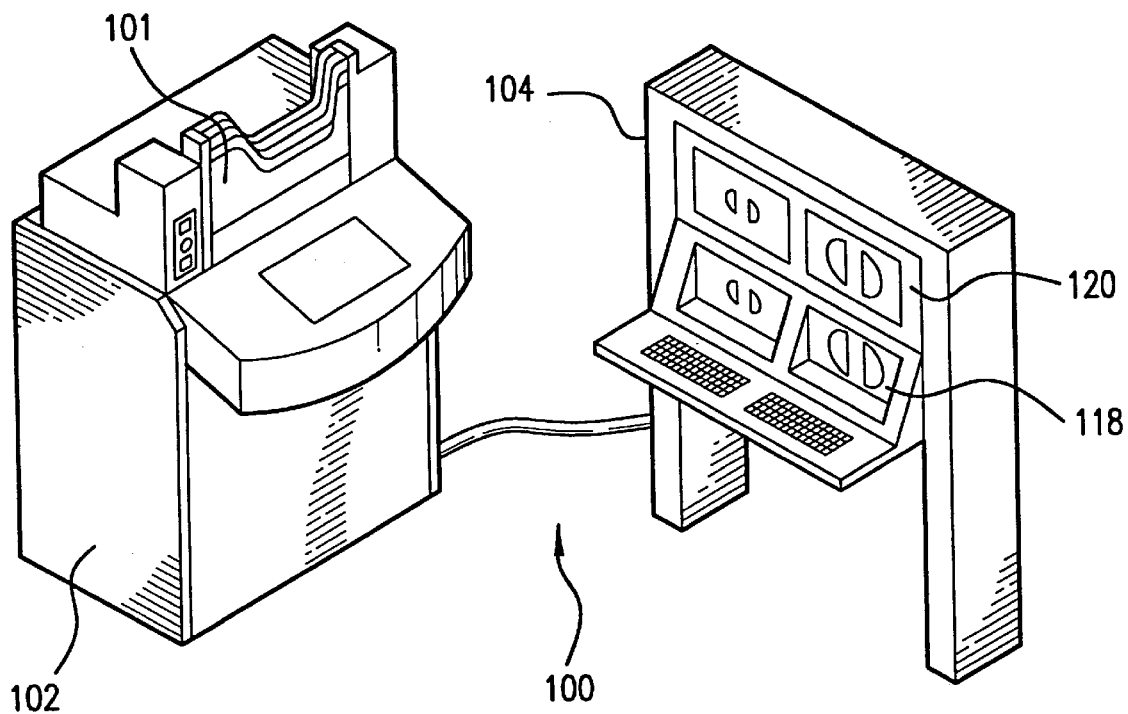
FIG. 1A shows an outside view of a computer aided diagnostic (CAD) system.
Figure 1B:
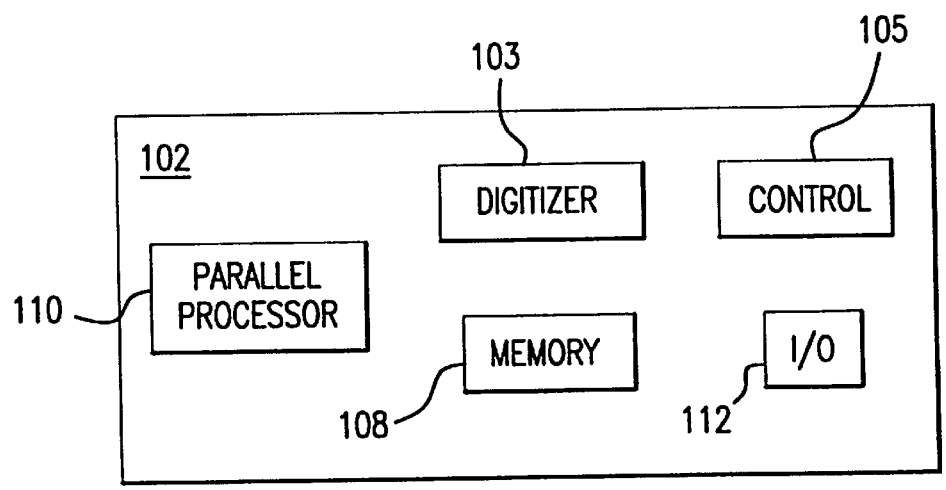
FIG. 1B shows a block diagram of CAD processing unit.

FIG. 1A shows an outside view of a computer aided diagnostic (CAD) system 100, such as the Image Checker M1000 from R2 Technology, Inc., for assisting in the identification of suspicious lesions in mammograms. CAD system 100 comprises a CAD processing unit 102 and a viewing station 104. In general, CAD processing unit 102 scans an x-ray mammogram into a digital mammogram image, processes the image, and outputs a highlighted digital mammogram for viewing at viewing station 104. FIG. 1B shows a block diagram of CAD processing unit 102. CAD processing unit 102 comprises a digitizer 103, such as a laser scanner with 50 micron resolution, for digitizing a developed x-ray mammogram 101, the x-ray mammogram 101 being shown in FIG. 1A at an input to the CAD processing unit 102. CAD processing unit 102 generally includes elements necessary for performing image processing including parallel processing steps. In particular, CAD processing unit 102 includes elements such as a central control unit 105, a memory 108, a parallel processing unit 110, and I/O unit 112. It is to be appreciated that the parallel processing unit 110 shown in FIG. 1B may be replaced by a single processor without departing from the scope of the preferred embodiments. It is to be appreciated that in addition to the suspicious lesion detection algorithms disclosed herein, processing unit 102 is capable of performing a multiplicity of other image processing algorithms either serially or in parallel therewith.

Viewing station 104 is for conveniently viewing both the x-ray mammogram 101 and the output of the CAD processing unit 102 on a display device 118. The display device 118 may be, for example, a CRT screen. The display device 118 typically shows a highlighted digital mammogram corresponding to the x-ray mammogram 101, the highlighted digital mammogram having information directing the attention of the radiologist to suspicious areas as determined by image processing steps performed by the CAD processing unit 102. In one preferred embodiment, the highlighted digital mammogram will have black or red circles superimposed around those locations corresponding to suspicious lesions. Viewing station 104 also comprises a backlighting station 120 for viewing the actual x-ray mammogram 101 itself. The radiologist is assisted by the CAD system 100 by viewing the display device 118, which then directs the attention of the radiologist to the suspicious portions of the actual x-ray mammogram 101 itself. Further information regarding CAD system 100 may be found in U.S. Pat. No. 5,815,591, supra.

It is to be appreciated that in addition to being able to display a single view of one breast, CAD system 100 may be used in accordance with the preferred embodiments to simultaneously display information related to multiple views of the same breast, similar views of opposing breasts, and/or views of a single breast taken at different points in time. Thus, the attention of the radiologist may be drawn to specific areas of a first mammogram image by CAD system 100, which can then be compared to corresponding areas of other views of the same breast, views of the opposing breast, or previous views of the same breast for making an appropriate determination.

Figure 2:
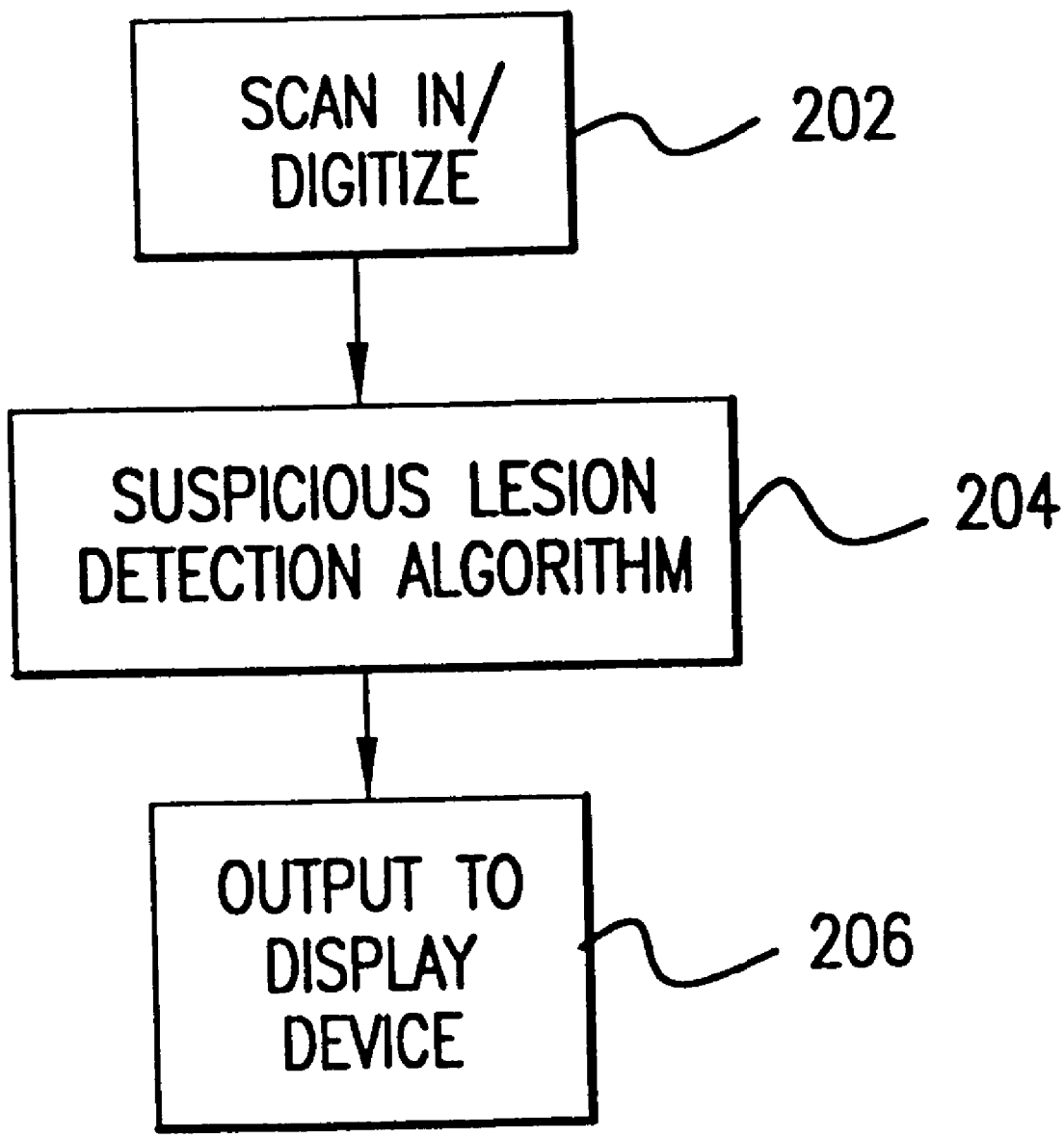
FIG. 2 shows overall steps performed by a CAD processing unit in accordance with a preferred embodiment.

FIG. 2 shows the general steps performed by CAD processing unit 102 on the x-ray mammogram. At step 202, multiple related x-ray mammograms are scanned in and digitized into digital mammograms. To create the x-rays mammograms, the breast is positioned and compressed between two plates before the X-ray is actually taken. Two views, corresponding to two approximately orthogonal orientations of the compression planes are taken, typically called craniocaudal (CC) view and mediolateral oblique (MLO) view. The resulting four films are developed, and digitized by the CAD system 100 to enable computer analysis at step 202. As an alternative to the manual x-ray development following by digitization step 202, the x-ray detector, which is presently usually a film screen cassette, can be replaced by a direct digital detector such as the General Electric Full Field Digital Mammography System, and the resulting digital image fed directly to the CAD processor unit 102.

While in one embodiment the multiple related x-ray mammograms correspond to two views of the same breast, e.g., the craniocaudal (CC) and the mediolateral oblique (MLO) view, in another embodiment the multiple related x-ray mammograms correspond to similar views of two opposing breasts, e.g., the MLO view of the left and right breast of a single subject. In yet another embodiment, there are three related x-ray mammograms wherein the first two are different views of the same breast, e.g., the CC and the MLO views, and the third being a view such as a the MLO view of the opposing breast. In still another embodiment, there is a fourth, historical x-ray mammogram corresponding to the first x-ray mammogram except that it has been taken months or years earlier in time that is entered into the CAD processing unit 102 for digitization. It is to be appreciated that there are further combinations of the above x-ray mammograms to be input into the CAD processing unit 102 that are within the scope of the preferred embodiments. It is to be further appreciated that the historical x-ray mammogram that was taken months or years earlier in time may have been stored in digitized form in CAD computer memory 108, or other digital storage medium, without departing from the scope of the preferred embodiments. Alternatively, to save storage space, only a historical set of feature vectors derived from prior digital mammograms may be stored in the CAD memory 108. Indeed, the CAD memory 108 or other storage medium may contain an entire historical archive of prior digital mammograms taken of the same breast or feature vectors derived therefrom, and CAD processing unit 102 may be modified to compare any of these historical digital mammograms or feature vectors derived therefrom to the current digital mammogram.

Each digital mammogram may be, for example, a 4000× 5000 array of 12-bit gray scale pixel values. Such a digital mammogram would generally correspond to a typical 18 cm×24 cm x-ray mammogram which has been digitized at a 50 micron spatial resolution. Because a full resolution image such as the 4000×5000 image described above is not always necessary for the effectiveness of the preferred embodiments, the image may be locally averaged, using steps known in the art, down to a smaller size corresponding, for example, to a 200 micron spatial resolution.

As shown in FIG. 2, the digital mammograms are processed at step 204 by an overall suspicious lesion detection algorithm in accordance with the preferred embodiments. As discussed previously, the overall lesion detection algorithms performed at step 204 generate a list of locations in at least one of the digital mammogram images which correspond to suspicious lesions, i.e. possibly cancerous lesions. Following step 204, the digital mammogram images and list of suspicious locations is sent for display to the viewing station 104 at step 206.

Figure 3:
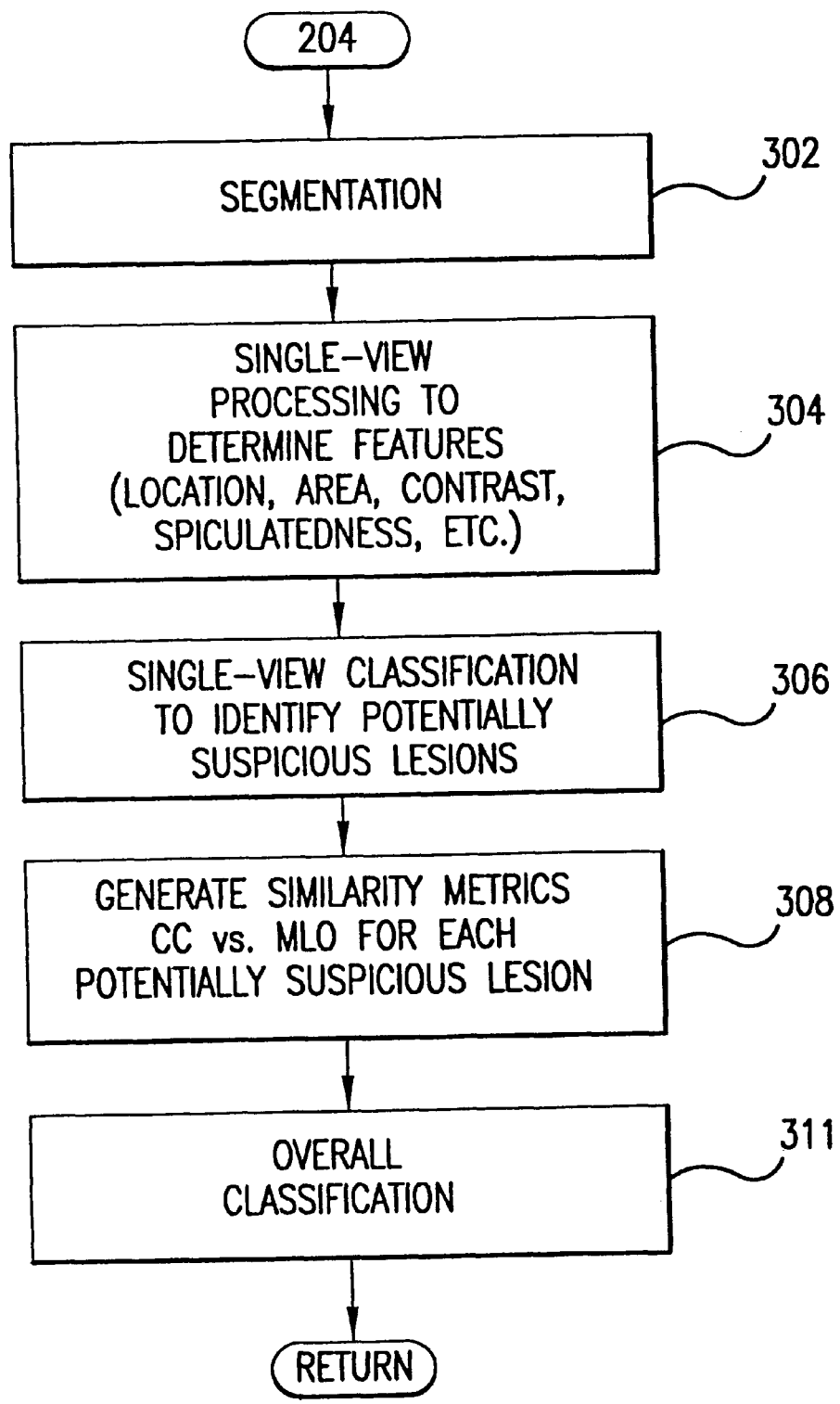
FIG. 3 shows steps for locating suspicious lesions using multiple digital mammogram views of a breast in accordance with a preferred embodiment.

FIG. 3 shows steps corresponding to step 204 for locating suspicious lesions in accordance with a preferred embodiment, wherein two views of the same breast are processed for identifying suspicious lesions in at least one of the views. In the example of FIG. 3, the two views processed are the craniocaudal view (CC) and the mediolateral oblique view (MLO), although other views of the same breast may be used in accordance with the preferred embodiments. At step 302 a segmentation algorithm is performed on each of the digital mammogram view, i.e., the CC and MLO views in this example. As known in the art, one purpose of segmentation is to specify reference locations from which positions in the breast may indexed. Among other features, the position of the chest wall and nipple are determined at step 302. In a preferred embodiment, locations of potentially suspicious lesions are then specified with respect to the chest wall and the nipple, although other positional metrics may be used as well. Importantly, location coordinates with respect to the chest wall and the nipple are carried across views of the same breast, as well as across views of opposing breasts, to when comparing features among the respective views.

At step 302, as an intermediate step in determining the position of the nipple, the skin line is segmented. Algorithms to locate the skin line have been described in the literature, one such method being described in U.S. Pat. No. 5,452,367 to Bick and Giger, the contents of which are hereby incorporated by reference into the present application. The nipple is expected to lie somewhere along the surface of the skin line.

Figure 4B:
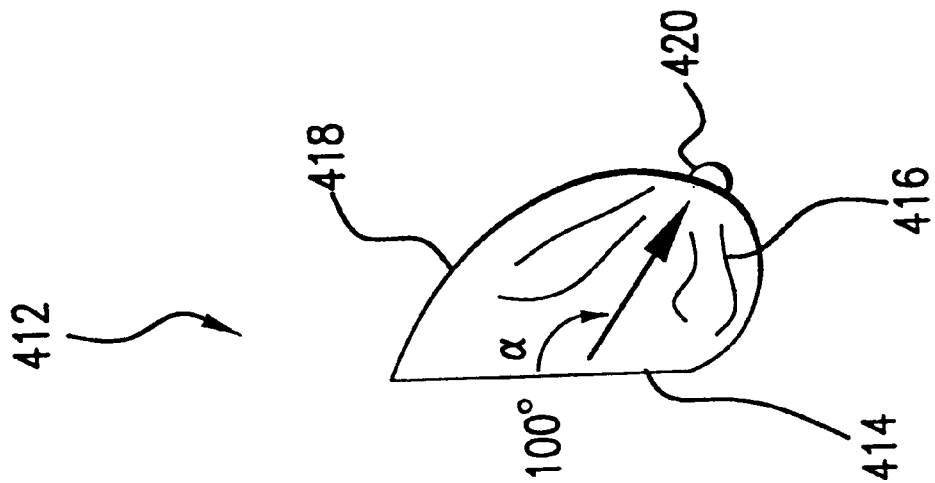
FIG. 4 shows sketches of two digital mammograms having different nipple positions.
Figure 4A:
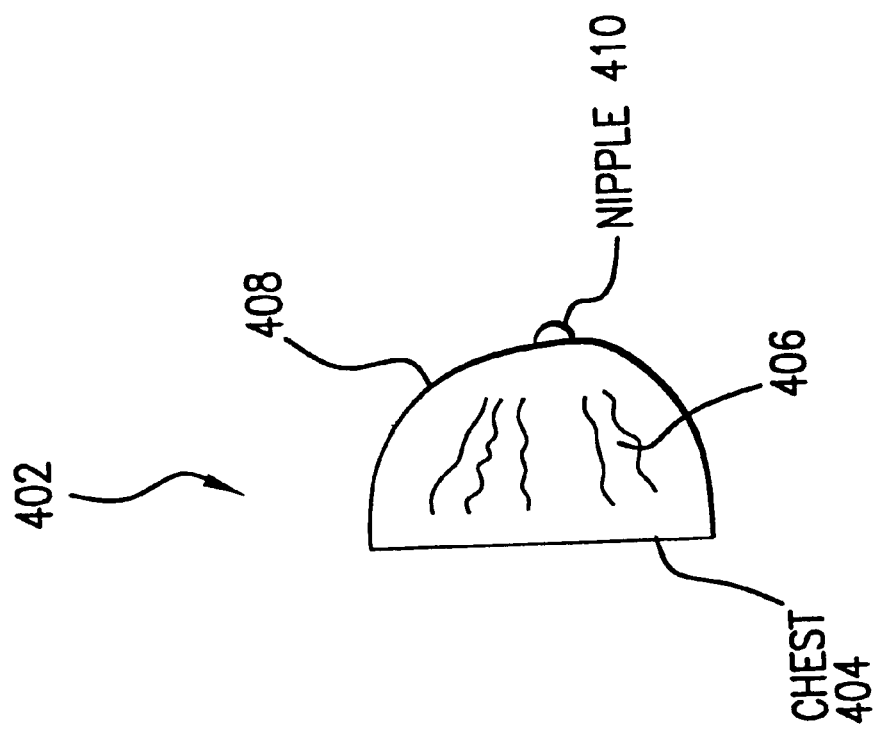

FIG. 4 shows an example of differing digital mammograms having different nipple positions relative to the skin line and chest wall. FIG. 4 shows a side view of an "ideal" digital mammogram 402 comprising a chest wall 404, fibrous tissue 406, a skin line 408, and a nipple 410. The digital mammogram 402 represents an "ideal" situation in that the nipple 410 is actually the point along skin line 408 that is farthest from the chest wall 404 in an orthogonal direction. Accordingly, in the ideal situation a CAD system can readily and accurately locate the position of nipple 410 by locating the point along skin line 408 that is farthest from the chest wall 404 in an orthogonal direction.

In practice, however, it is often found that the true position of the nipple varies significantly from the position of nipple 410 in FIG. 4 due to imperfect positioning, compression, or manipulation of the breast during the x-ray mammography process. FIG. 4 also shows a practical digital mammogram 412 comprising a chest wall 414, fibrous tissue 416, a skin line 418, and a nipple 420. As shown in FIG. 4, nipple 420 is at a substantially different position than the "ideal" position. It has been found that a statistically significant number of prominent lines in the fibrous tissue 416 tend to point toward the true position of the nipple 420 in practical digital mammograms. This is shown generally by an arrow positioned at an angle ALPHA with respect to the chest wall 414 in the practical digital mammogram 412. If a histogram of the directions of all large lines (ducts) is computed, a peak is generally evident in the direction pointing to the nipple, the peak being at approximately 100 degrees in the practical example of FIG. 4.

Figure 5:
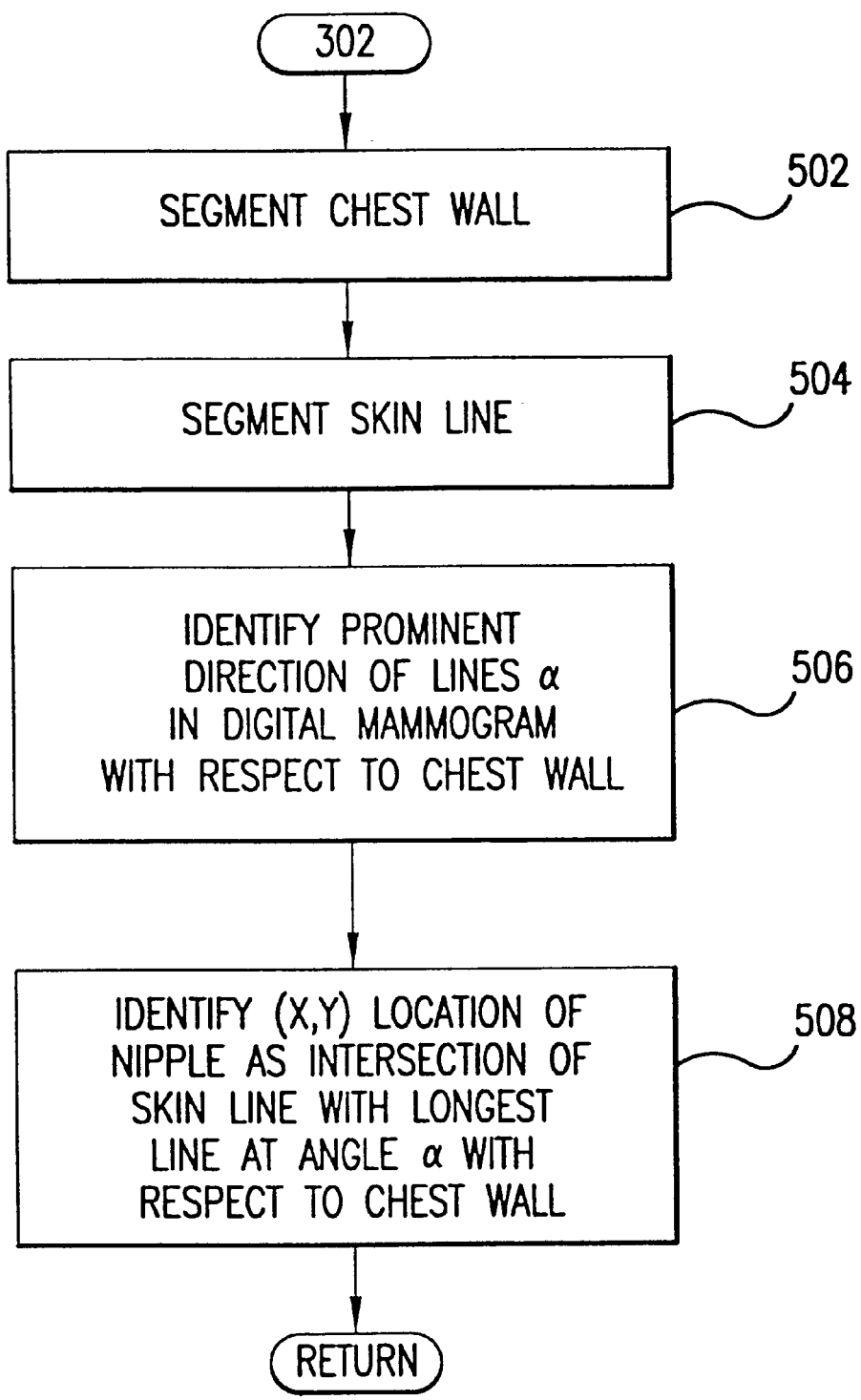
FIG. 5 shows steps for identifying nipple location in accordance with a preferred embodiment.

FIG. 5 shows steps taken during the segmentation step 302 to locate the (x,y) position of the nipple 420 in accordance with a preferred embodiment. At step 502 the chest wall is segmented using methods known in the art. At step 504, the skin line is segmented using steps known in the art, as described supra. At step 506 the prominent direction of lines $\alpha$ are identified in the digital mammogram with respect to the chest wall. The computation of the most prominent direction of lines may be computed using histogram-based plotting methods or other methods known in the art. Finally, at step 508, the (x,y) location of the nipple is determined as the intersection of the skin line with the longest line that can be drawn between the chest wall and the skin line at an angle $\alpha$ with respect to the chest wall. In this fashion, the nipple position is more reliably and accurately determined, the nipple position being of importance because it serves as a reference or index point for specifying locations of potentially suspicious breast lesions in the digital mammograms being compared.

Once the locations of the chest wall and nipple are determined at step 302, positions in the digital mammogram views may then be referenced with respect to the chest wall and/or nipple for purposes of feature comparison. These reference positions are used for feature comparisons different views of the same breast, as well in feature comparison among views of opposing breasts. In one preferred embodiment, feature position is specified by the coordinates $(d_w, \Delta x, \Delta y)$, where $d_w$ represents distance from the chest wall, and where $\Delta x$ and $\Delta y$ represent distances from the nipple position. In another preferred embodiment, feature position may be specified by the $(\Delta x, \Delta y)$ coordinates alone. In still another embodiment, it has been found that the direct radial distance from the nipple alone, $R_{NIPPLE}$, is a sufficient location metric to produce acceptable results for feature comparisons. For simplicity and clarity purposes, and without limiting the scope of the preferred embodiments, the remainder of this disclosure uses the simple scalar quantity $R_{NIPPLE}$ as the position metric for feature comparison purposes.

Subsequent to the segmentation step 302, a single-view feature vector computation step 304 is performed, wherein each digital mammogram view is separately processed for computing single-view feature vectors associated therewith. The specific feature vectors computed at step 304 depend on which overall suspicious lesion detection algorithm is employed. Any of a number of available algorithms may be used for the purpose of determining suspicious lesions in a single digital mammogram view including, but not limited to: U.S. Pat. No. 5,815,591 to Roehrig et. al.; U.S. patent application No. 08/868,277 to Karssemeijer et. al. filed Jun. 3, 1997; U.S. Pat. No. 5,657,362 to Giger et al; U.S. Pat. No. 5,491,627 to Zhang et al; U.S. Pat. No. 5,537,485 to Nishikawa et al; and te Brake and Karssemeijer, Detection of Stellate Breast Abnormalities, Digital Mammography 1996, K. Doi, Mary Ellen Giger, Robert Nishikawa, R. Schmidt, eds., the contents of which are incorporated by reference into the present application. It is necessary that the chosen algorithm be designed to yield substantially correct results on "true" lesions with reasonable sensitivity and with as few spurious markers as possible. In a preferred embodiment, an area feature corresponding to the lesion area should also be computed, regardless of whether it is needed by the single-view lesion detection algorithm used. The area metric may become important in cross-view feature comparison steps, as further described infra.

The results of the single-view feature computation step 304 include a plurality of feature vectors for each digital mammogram view. Often, depending on the single-view lesion detection algorithm chosen, there are many such feature vectors. There may be fewer feature vectors, however, if the selected single-view lesion detection algorithm is designed to discard feature vectors "on the fly" upon an on-the-spot-determination that a region or pixel will never be interesting. Although the contents of the feature vectors will vary depending on the particular single-view algorithm or algorithms used, each feature vector may contain, for example, the following features: location (e.g., the distance $R_{NIPPLE}$, described supra); area; contrast; spiculatedness; and eccentricity. It is to be understood that there may be a greater number or a lesser number of elements in the feature vectors without departing from the scope of the preferred embodiments, and that the type of metrics contained in the feature vectors may also be different than in the above example.

At step 306, the single view feature vectors are processed in a classification algorithm to identify potentially suspicious lesions in the respective single-view digital mammograms. It is to be appreciated that step 306 may be combined with step 304 in some algorithms for which feature vector computation and lesion detection take place in a single step. The classification scheme used to identify potentially suspicious lesions at step 306 in each of the digital mammogram views may be any of a variety of classification algorithms including neural network algorithms, linear classifier algorithms, quadratic classifier algorithms, etc.

Upon completion of step 306, CAD processing unit 102 contains two sets of feature vectors, one set for each of the CC and MLO views, as illustrated below in TABLE 1.

TABLE 1

| MLO VIEW | CC VIEW |
| --- | --- |
| [$f_{01}\ f_{11}\ f_{21}\ f_{31}$] | [$g_{01}\ g_{11}\ g_{21}\ g_{31}$] |
| [$f_{02}\ f_{12}\ f_{22}\ f_{32}$] | [$g_{02}\ g_{12}\ g_{22}\ g_{32}$] |
| [$f_{03}\ f_{13}\ f_{23}\ f_{33}$] | [$g_{03}\ g_{13}\ g_{23}\ g_{33}$] |
| [$f_{04}\ f_{14}\ f_{24}\ f_{34}$] | [$g_{04}\ g_{14}\ g_{24}\ g_{34}$] |
| ... (etc.) | ... (etc.) |

In TABLE 1, the MLO feature vectors are designated as follows: for the $i^{th}$ potentially suspicious lesion, the related feature vector is denoted [ $f_{0i}\ f_{1i}\ f_{2i}\ f_{3i}$ ], where $f_{0i},\ f_{1i},\ f_{2i},$ and $f_{3i}$ are each scalar feature metrics for the $i^{th}$ potentially suspicious lesion. Likewise, for the $i^{th}$ potentially suspicious lesion in the CC view, the related feature vector is denoted [ $g_{0i}\ g_{1i}\ g_{2i}\ g_{3i}$ ], where $g_{0i},\ g_{1i},\ g_{2i},$ and $g_{3i}$ are the same type of feature metrics as $f_{0i},\ f_{1i},\ f_{2i},$ and $f_{3i}$ except they are measured in the CC view. By way of non-limiting example, in the embodiment of FIG. 3 and TABLE 1, $f_{0i}$ represents the distance $R_{NIPPLE}$ if the $i^{th}$ potentially suspicious lesion from the nipple; $f_{1i}$, represents the area of the $i^{th}$ potentially suspicious lesion; $f_{2i}$ represents the contrast of the $i^{th}$ potentially suspicious lesion; and $f_{3i}$ represents a spiculatedness measure associated with the $i^{th}$ potentially suspicious lesion computed, for example, using the method of U.S. Pat. No. 5,815,591, supra.

Importantly, it is to be understood that the feature vectors of TABLE 1 may contain all of the metrics, or just a portion of the metrics, computed at steps 304–306. Moreover, it is to be appreciated that the feature vectors shown in TABLE 1 may contain a greater or fewer number of metrics than the exemplary value of four, and that the nature of the individual metrics may be different than location, area, contrast, and spiculatedness. For example, in one preferred embodiment, only a location metric, an area metric and a contrast metric are used. In another preferred embodiment, an additional metric is used corresponding to the single-view probability of suspiciousness as determined at step 306. Finally, it is to be appreciated that although the feature vector elements $f_{0i},\ f_{1i},\ f_{2i},$ and $f_{3i}$ are scalars in the above example, one or more of these elements may in themselves be vectors or matrices without departing from the scope of the preferred embodiments.

At step 308, a similarity metric is computed between each MLO feature vector and each CC feature vector. In relation to step 308, the preferred embodiments are based at least in part on the finding that correlation of a true lesion between CC and MLO views is only approximate, because suboptimal breast positioning of the two images will cause the lesion position to differ somewhat in the two images. Sometimes, especially when the lesion is close to the chest wall, the lesion will fail to appear at all in one view due to the breast not be pulled out enough in that view, but still appear in the other view. An automated lesion detection method that exploits multiple view correlation should use cross-view correlations in a softer or more analogue manner, rather than in a hard binary yes/no manner.

Accordingly, at step 308 a similarity metric is computed between each MLO feature vector and each CC feature vector. Each similarity metric takes the form of a cost function measured as the weighted distance between two feature vectors in feature vector space. An exemplary form of the cost function, shown between the $j^{th}$ MLO feature vector and the $k^{th}$ CC feature vector and represented by the symbol $C_{jk}$ is shown in Eq. 1.

$$C_{jk} = \sqrt{a_0(f_{0j} - g_{0k})^2 + a_1(f_{1j} - g_{1k})^2 + a_2(f_{2j} - g_{2k})^2 + a_3(f_{3j} - g_{3k})^2} \qquad \text{Eq. 1}$$

Each potentially suspicious lesion in the MLO view will have N associated similarity metrics, where N corresponds to the number of potentially suspicious lesions that were identified from the CC view. Each of the respective similarity metrics computed by Eq. 1 is equal to a Euclidean distance in weighted form between the feature vector in the MLO view and each feature vector in the CC view as measured in feature space. It is easily seen from Eq. 1 that the similarity metric between two potentially suspicious lesions will be smaller if their respective feature vector metrics are very similar, i.e., if their characteristics are similar, whereas the similarity metric will be greater if the two potentially suspicious lesions are not similar.

It is to be appreciated that the cost functions shown in Eq. 1 that is used as the similarity metric is only one of a representative sample of many different cost functions which may be used in accordance with a preferred embodiment. Generally speaking, any cost function representing a feature space distance between two feature vectors can be used if it will have a global extremum, e.g., a minimum value, when two feature vectors are identical to each other, and a monotonic character moving away from the extremum as the feature vectors get further away from each other.

Assuming normalization of features, the relative sizes of coefficients $a_0,\ a_1,\ a_2,$ and $a_3$ are determined by the relative importance of the features, which is empirically determined. The most important feature will be assigned the largest coefficient, the next most important feature the next largest coefficient, and so on down to the least important feature, which is assigned the smallest coefficient. The number of features from the single-view feature vectors that will actually be used, or equivalently, how many of the coefficients $a_n$ have significant magnitude, is also empirically determined and may vary as the algorithm is refined. The empirically determined useful features according to a preferred embodiment use the nipple distance $R_{NIPPLE}$ as the most important feature, region size or area as the second feature element, and single-view probability from the first single image classifier as the third feature vector element.

It is also found that two distances, one from the nipple ($R_{NIPPLE}$) and one from the chest wall ($d_w$), appear to be useful because occasionally the nipple distance is difficult to determine and there may be a large error. Also, if the lesion happens to be close to the chest on a large breast, the chest wall distance $d_w$ appears to have less error than the nipple distance $R_{NIPPLE}$. However, sometimes due to poor positioning in one view, the chest wall distance $d_w$ may be abnormally large, in this case the nipple distance $R_{NIPPLE}$ is more reliable.

The area of the lesion is important as a feature exists for at least two reasons. First, the area of a true lesion seems to maintain itself across views very well. Second, the area of the lesion is not used in a single-view lesion detection algorithm. Area is a new piece of information that becomes useful only when comparing two views because true lesions come in a spectrum of sizes from small to large. Size in itself is not an indicator of whether the lesion is true when looking at a single view. Hence, area itself is not an important indicator of trueness, but the difference in area between two views is an important indicator showing consistency between the views. Finally, the single-view suspiciousness probability is important because there are a number of single-view features that are highly correlated to "trueness" of a lesion.

As indicated previously, it is to be appreciated that not all feature metrics computed at step 304 need to be used in generating the similarity metrics at step 308. Indeed, in a simpler implementation in accordance with a preferred embodiment, there are only two features used in the computation of the similarity metrics: (1) $f_{0i}=R_{NIPPLE}$, and (2) $f_{1i}$=area. In this preferred embodiment, it has been empirically found that appropriate weights across views are $a_0=1.0$, and $a_1=0.2$. It is to be appreciated that if all coefficients are set to zero except for $a_0$, the distance in feature vector space actually becomes a true physical distance difference, equal to the difference between $R_{NIPPLE}$ in the MLO view and $R_{NIPPLE}$ in the CC view.

At step 311, an overall classification algorithm is used to determine the suspicious lesions to output to the display 118. The classification algorithm used at step 311 may be any of a variety of algorithms, but importantly will have inputs corresponding to (1) the feature vectors computed at steps 304–306, and (2) the similarity metrics computed at step 308. In this manner, a CAD system 100 in accordance with the preferred embodiment is capable of using information from both single view feature vectors as well as information from a comparison of two views of the same breast, to arrive at a final determination of suspiciousness. The classification algorithm at step 311 may be any of a variety of classifiers, provided that it is appropriately influenced by both the single-view feature vectors and the similarity metrics. Other factors being equal, the overall probability of suspiciousness should be greater where the similarity metric reflects a high degree of similarity between corresponding lesions in two views.

Advantageously, in accordance with a preferred embodiment, there are no "hard" or "yes/no" decisions associated with single view information or comparison information separately. Rather, the information is all fed into a classification algorithm at step 311 for a final determination to be made. In this way, it is possible that even though there is very little correspondence between two views of the same breast for a given lesion, this lesion may still be identified as an overall suspicious lesion, if the single view feature vectors indicate a very strong probability of suspiciousness. Advantageously, steps taken in accordance with the preferred embodiments are designed to approximate the thought process that a human mammographer will perform when searching for lesions, while maintaining as low a work up rate (the rate at which routine screening mammograms call for further workup such as spot compression, magnification views, ultrasound, etc.) is possible.

Figure 6:
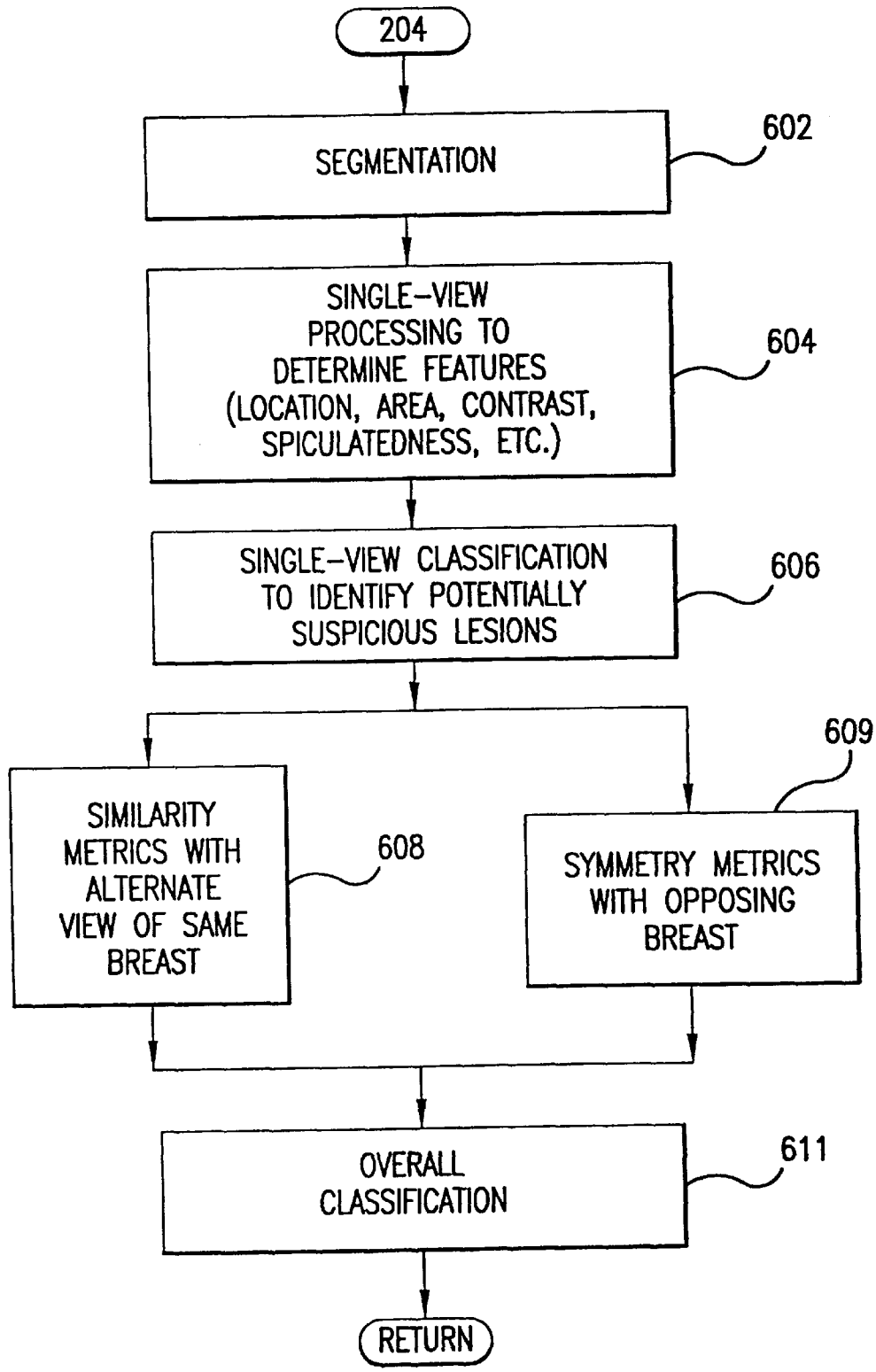
FIG. 6 shows steps for locating suspicious lesions using multiple digital mammogram images in accordance with a preferred embodiment.

FIG. 6 shows steps corresponding to step 204 for locating suspicious lesions in accordance with another preferred embodiment in which, in addition to the computation of similarity metrics from alternate views of the same breast, a set of symmetry metrics are computed from views of opposing breasts. As shown in FIG. 6, the steps 602, 604, and 606 are carried out in a manner similar to the steps 302, 304, and 306 of FIG. 3, except that a digital mammogram view of the opposing breast is processed in addition to the MLO and CC views of the first breast. By way of non-limiting example, the MLO view of the opposing breast is used in the embodiment of FIG. 6, although other views may be used. Included in the results of steps 604–606 is an additional set of feature vectors [ $h_{0i}$ $h_{1i}$ $h_{2i}$ $h_{3i}$ ], where $h_{0i}$, $h_{1i}$, $h_{2i}$, and $h_{3i}$ are the same type of feature metrics as $f_{0i}$, $f_{1i}$, $f_{2i}$, and $f_{3i}$ except they are measured in the MLO view of the opposing breast.

As shown in FIG. 6, an additional step 609 is carried out in parallel with the step 608, wherein a set of symmetry metrics between the MLO view of the first breast and the MLO view of the opposing breast is computed. In relation to step 609, the preferred embodiments are based at least in part on the finding that symmetry between left and right breasts is only approximate even when the breasts are positioned perfectly. The tissue structure in the two breasts will always differ somewhat. Hence, the importance of a determination that a density on one breast is or is not mirrored in the other breast, and to what degree, is a relative judgment best incorporated in a symmetry metric in accordance with the preferred embodiments.

Thus, at step 609, symmetry metrics between a digital mammogram of the opposing breast are computed between the first digital mammogram (eg, the MLO view of the first breast) and a corresponding view of the opposing breast. It is to be appreciated that while MLO-MLO symmetry metrics are computed at step 609, it is not necessary to compare similar views of the opposing breast in order to be within the scope of the preferred embodiments. It is permissible that a third view of the opposing breast may be used that does not correspond to either of the views used for the first breast, although the preferred embodiment as disclosed herein shows identical views of opposing breasts being processed. The steps used to compute the symmetry metrics at steps 609 are similar to the steps used to compute the similarity metrics at step 608 except that feature vectors [ $h_{0i}$ $h_{1i}$ $h_{2i}$ $h_{3i}$ ] from the opposing breast are used. TABLE 2 and Eq. 2 below illustrate the step 609 of computing the symmetry metrics.

TABLE 2

| MLO - Breast 1 | MLO - Opposing Breast |
|---|---|
| [$f_{01}$ $f_{11}$ $f_{21}$ $f_{31}$] | [$h_{01}$ $h_{11}$ $h_{21}$ $h_{31}$] |
| [$f_{02}$ $f_{12}$ $f_{22}$ $f_{32}$] | [$h_{02}$ $h_{12}$ $h_{22}$ $h_{32}$] |
| [$f_{03}$ $f_{13}$ $f_{23}$ $f_{33}$] | [$h_{03}$ $h_{13}$ $h_{23}$ $h_{33}$] |
| [$f_{04}$ $f_{14}$ $f_{24}$ $f_{34}$] | [$h_{04}$ $h_{14}$ $h_{24}$ $h_{34}$] |
| ... (etc.) | ... (etc.) |

$$D_{jk} = \sqrt{b_0(f_{0j} - h_{0k})^2 + b_1(f_{1j} - h_{1k})^2 + b_2(f_{2j} - h_{2k})^2 + b_3(f_{3j} - h_{3k})^2} \quad \text{Eq. 2}$$

The symmetry metrics for each potentially suspicious lesion in the MLO view of the first breast correspond to the cost functions $D_{jk}$ in Eq. 2. It is to be appreciated that the weights $b_0$, $b_1$, $b_2$, and $b_3$ are generally different than the weights $a_0$, $a_1$, $a_2$, and $a_3$ used to compute similarity metrics at step 608. However, the empirical methods for deriving their values are generally similar. As with the steps taken at step 608, a given cost function $D_{jk}$ will be small when the associated potentially suspicious lesions are similar, i.e., have similar feature vector metrics, and will be greater when the lesions are not similar. Also as with step 608, the constant $b_0$ associated with the first element of the feature vector, which is the nipple distance $R_{NIPPLE}$, will generally be the largest weight afforded in Eq. 2. This is because, as intuitively suspected, the location of a lesion in one view is generally the most important factor in determining whether it corresponds to a lesion in another view.

At step 611, an overall classification algorithm is used to determine the suspicious lesions to output to the display 118. The classification algorithm used at step 611 may be any of a variety of algorithms, but importantly will have inputs corresponding to (1) the feature vectors computed at steps 604–606, and (2) the similarity metrics computed at step 608, and (3) the symmetry metrics computed at step 609. Other factors being equal, the overall probability of suspiciousness for a given lesion should be reduced when there exists a symmetric feature in the opposing breast, as indicated by a low symmetry metric.

Figure 7:
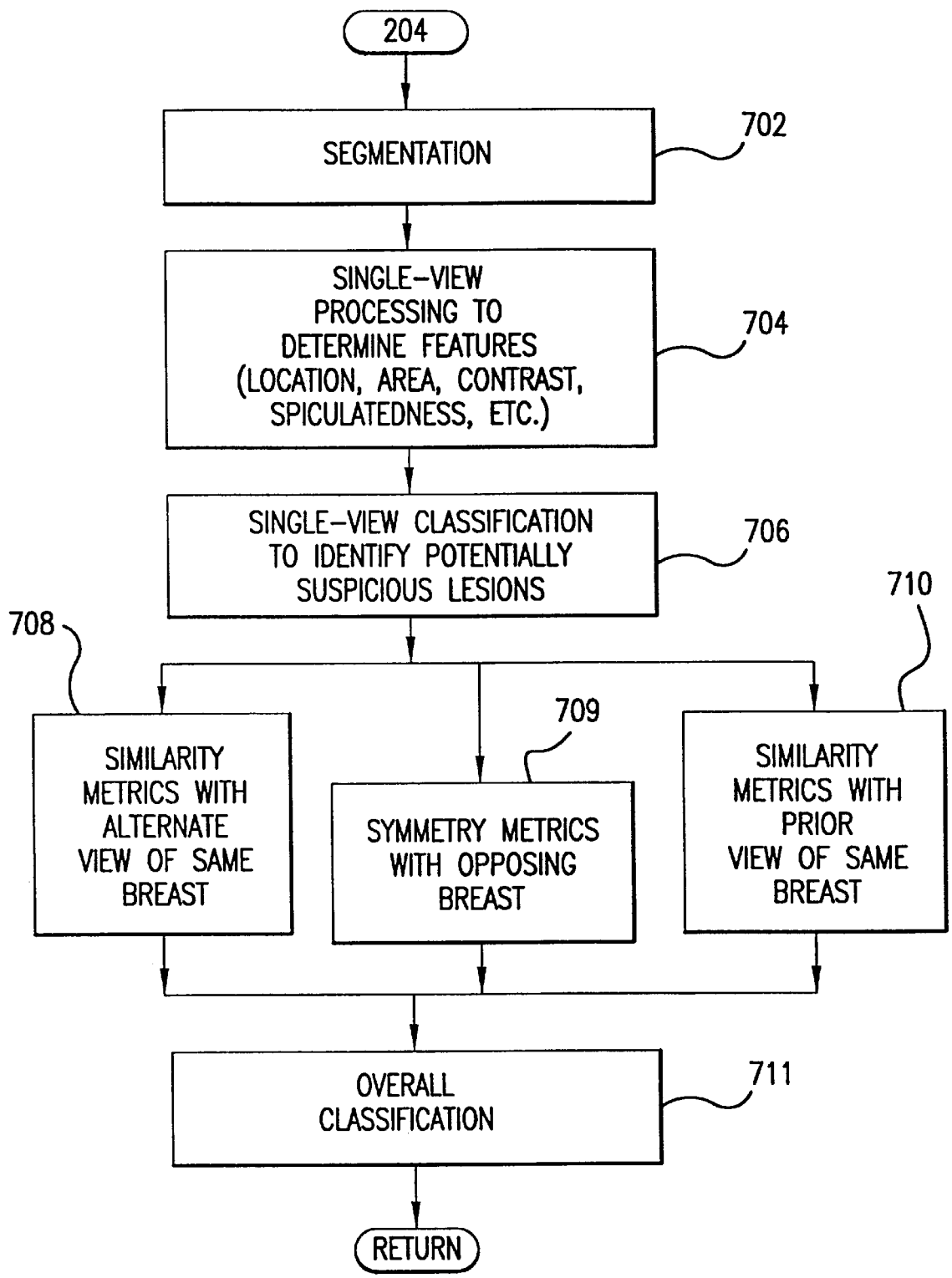
FIG. 7 shows steps for locating suspicious lesions using multiple digital mammogram images in accordance with a preferred embodiment.

FIG. 7 shows steps corresponding to step 204 for locating suspicious lesions in accordance with another preferred embodiment in which, in addition to the computation of similarity metrics from alternate views of the same breast and symmetry metrics computed from views of opposing breasts, a set of similarity metrics with a prior view of the breast is computed. Generally speaking, the prior digital mammogram was taken 6–12 months before the current digital mammogram, but the scope of the preferred embodiments is not so limited.

In the algorithm of FIG. 7, steps 702, 704, 706, 708 and 709 are carried out in a manner similar to steps 602, 604, 606, 608 and 609 of FIG. 6. By way of non-limiting example, a prior MLO view of the breast is used, although other views may be used. Included in the results of steps 704–706 is an additional set of feature vectors [ $P_{0i}$ $P_{1i}$ $P_{2i}$ $P_{3i}$ ], where $P_{0i}$, $P_{1i}$, $P_{2i}$, and $P_{3i}$ are the same type of feature metrics as $f_{0i}$, $f_{1i}$, $f_{2i}$, and $f_{3i}$ except they are measured in the prior MLO view.

As shown in FIG. 7, an additional step 710 is carried out in parallel with the steps 708 and 709, wherein a set of similarity metrics between the current MLO view of the first breast and the prior MLO view of the first breast is computed. In relation to step 710, the preferred embodiments are based at least in part on the finding in temporal subtraction, one looks for change in the lesion from prior examination to current examination. But this, too, is only approximate—one must allow some difference in lesion position due to slightly differing compression and positioning. Also, one may consider the current year lesion to be more suspicious not only if a change occurred, such as size, number of calcifications etc., but even regardless of change, if the probability from a single view is high enough. Hence, the importance of a determination that a density in a breast has changed or has not changed in the last 12 months, and to what degree, is a relative judgment best incorporated in a similarity metric in accordance with the preferred embodiments.

The steps used to compute the similarity metrics at step 710 are similar to the steps used to compute the similarity metrics at step 608 except that feature vectors [ $P_{0i}$ $P_{1i}$ $P_{2i}$ $P_{3i}$ ] from the prior MLO view are used. TABLE 3 and Eq. 3 below illustrate the step 710 of computing the similarity metrics.

TABLE 3

| MLO - Breast 1 (current) | MLO - Breast 1 (prior) |
|---|---|
| [$f_{01}$ $f_{11}$ $f_{21}$ $f_{31}$] | [$p_{01}$ $p_{11}$ $p_{21}$ $p_{31}$] |
| [$f_{02}$ $f_{12}$ $f_{22}$ $f_{32}$] | [$p_{02}$ $p_{12}$ $p_{22}$ $p_{32}$] |
| [$f_{03}$ $f_{13}$ $f_{23}$ $f_{33}$] | [$p_{03}$ $p_{13}$ $p_{23}$ $p_{33}$] |
| [$f_{04}$ $f_{14}$ $f_{24}$ $f_{34}$] | [$p_{04}$ $p_{14}$ $p_{24}$ $p_{34}$] |
| ... (etc.) | ... (etc.) |

$$E_{jk} = \sqrt{c_0(f_{0j} - p_{0k})^2 + c_1(f_{1j} - p_{1k})^2 + c_2(f_{2j} - p_{2k})^2 + c_3(f_{3j} - p_{3k})^2} \quad \text{Eq. 3}$$

The similarity metrics for each potentially suspicious lesion in the MLO view of the current breast correspond to the cost functions $E_{jk}$ in Eq. 2. It is to be appreciated that the weights $c_0$, $c_1$, $c_2$, and $C_3$ are generally different than the weights $a_0$, $a_1$, $a_2$, and $a_3$ used to compute similarity metrics at step 708 and the weights $b_0$, $b_1$, $b_2$, and $b_3$ used to compute the symmetry metrics at step 709. However, the empirical methods for deriving their values are generally similar. It is expected that, if the breast has not changed over the period of the year between mammogram screenings, there will be an identical potentially suspicious lesion in the prior mammogram for each potentially suspicious lesion in the current mammogram. Accordingly, for each of the potentially suspicious lesions found at step 704 for the current mammogram, it is expected that there will be at least one very low similarity metric found with respect to the prior view of the same breast.

At step 711 an overall classification algorithm is performed in a manner similar to the classification step 611 in FIG. 6. However, other factors being equal, the probability of suspiciousness is increased if, for any potentially suspicious lesion in the first view of the current mammogram, there is not a low similarity metric found in relation to the prior view of the same breast.

It is to be appreciated that additional embodiments exist that are within the scope of the preferred embodiments. Most importantly, within the scope of the preferred embodiments is a CAD system in which only step 710 (prior view) is carried out between step 706 and step 711 in FIG. 7, without the performance of steps 708 (alternate view of same breast) and 709 (view of opposing breast). Such a CAD system would have the purpose of exclusively looking at single view feature vectors, together with similarity metrics with a prior view of the same breast, for determining overall suspiciousness. Likewise, in another preferred embodiment, only the two steps 710 (prior view) and step 708 (alternate view of same breast) may be carried out between step 706 and step 711 in FIG. 7, while step 709 (opposing breast) is not performed. Generally speaking, any single one of the steps 708 (alternate view of same breast), 709 (opposing breast), or 710 (prior view), or any combination thereof, may be performed within the scope of the preferred embodiments.

FIGS. 8–11 are directed to techniques for selecting empirical parameters associated with the computation of the symmetry and similarity functions described supra. It is to be appreciated that one of skill in the art would be able to generate and experimentally determine the empirical parameters $a_0$–$a_3$, $b_0$–$b_3$, and $c_0$–$c_3$ and other parameters using methods known in the art in conjunction with reviewing the present disclosure. FIGS. 8–11 simply display one method of determining optimal parameter values that may be modified as needed by the person skilled in the art as dependent on the goals and specific parameters of a particular CAD system.

Figure 8:
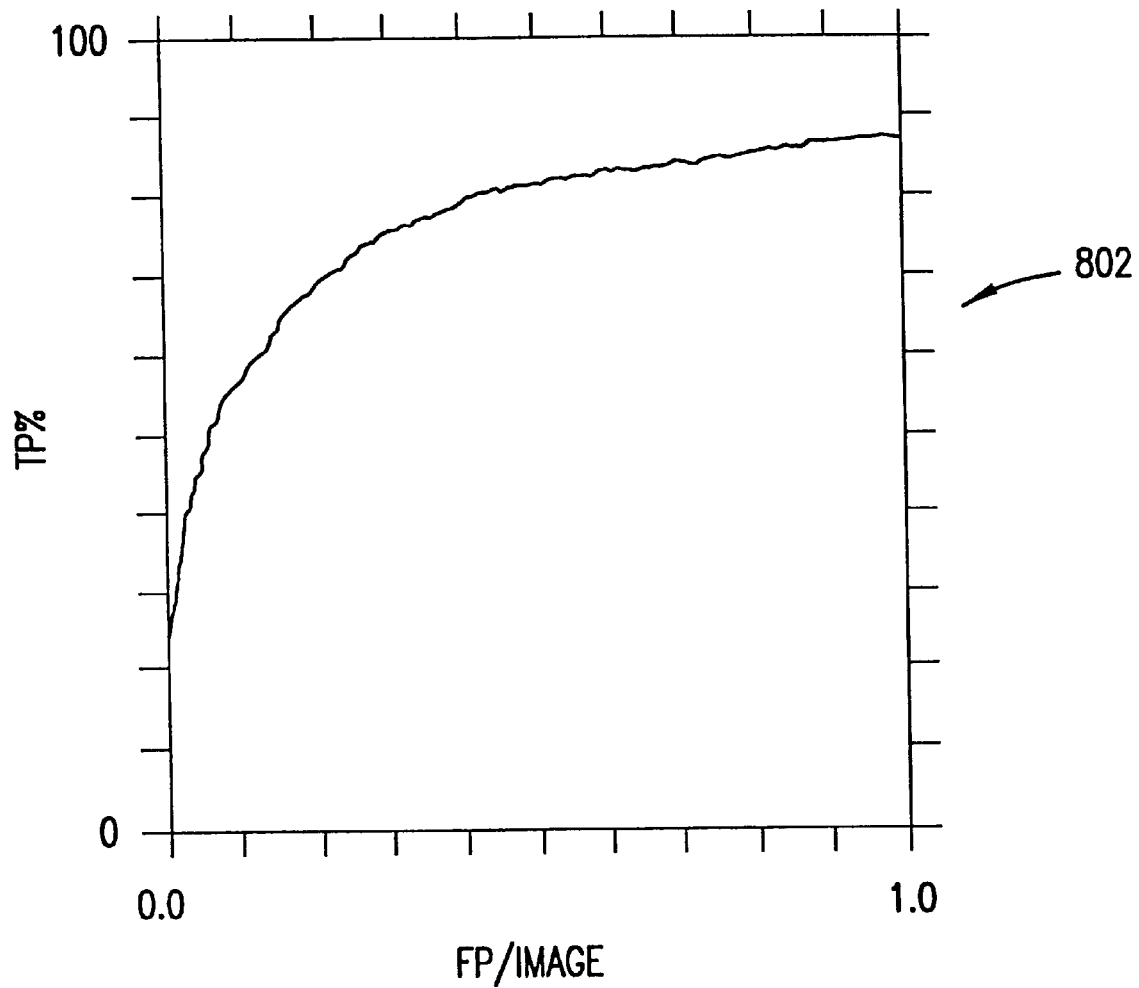
FIG. 8 shows an FROC curve corresponding to a computer-aided lesion detection device.

FIG. 8 shows an FROC curve 802 corresponding to a computer-aided lesion detection device that shows percentage of true positives on the ordinate axis and false positives per image on the horizontal or abscissa axis. As known in the art, the FROC curve is a quality measure for a given system and/or algorithm used by the system. The FROC curve is computed using a large set of digital mammograms, usually more than 100, for which the actual number and positions of true lesions are already known and identified. For a first level of sensitivity, as determined by setting a sensitivity-affecting variable such as the threshold parameter in the linear classifier algorithm at a first level, the lesion detection algorithm is run these 100 digital mammograms. The plurality of areas marked as "suspicious" by the lesion detection algorithm are then manually examined. The number of false positives is recorded, i.e. the number of areas marked "suspicious" which, in reality, are not suspicious at all and are not one of the pre-known true lesions. Then, the number of true positives are detected, i.e. the number of areas marked "suspicious" which actually are suspicious because they are one of the pre-known true lesions. A point is then plotted on FIG. 8, the abscissa corresponding to the number of false positives per image, and the ordinate corresponding to the percentage of true positives. The process is then repeated for many values of the sensitivity-affecting variable, resulting in the FROC curve 802 shown in FIG. 8.

Reading the FROC curve of FIG. 8, one can see that, for example, when the parameters are adjusted to yield 0.5 of false positives per image, the number of the percentage of true positives that are recognized, also called sensitivity, is about 81%. If the parameters are changed to increase the sensitivity, for example up to 85%, it is found that the number of false positives per images becomes 0.8. Generally speaking, it is desirable that the FROC curve 802 for a given system be upward and as far to the left as possible in FIG. 8. One simple measure of quality based on the FROC curve that could be used for comparison purposes would simply be the value of TP at a fixed value of FP/Image. The higher this value, the better the system. A different measure of quality, more comprehensive than the first, could be the integral of the FROC curve from FP/Image=0 to a predetermined point along the abscissa, for example, FP/Image=0.4. The greater the value of that integral, the better the system.

Figure 9:
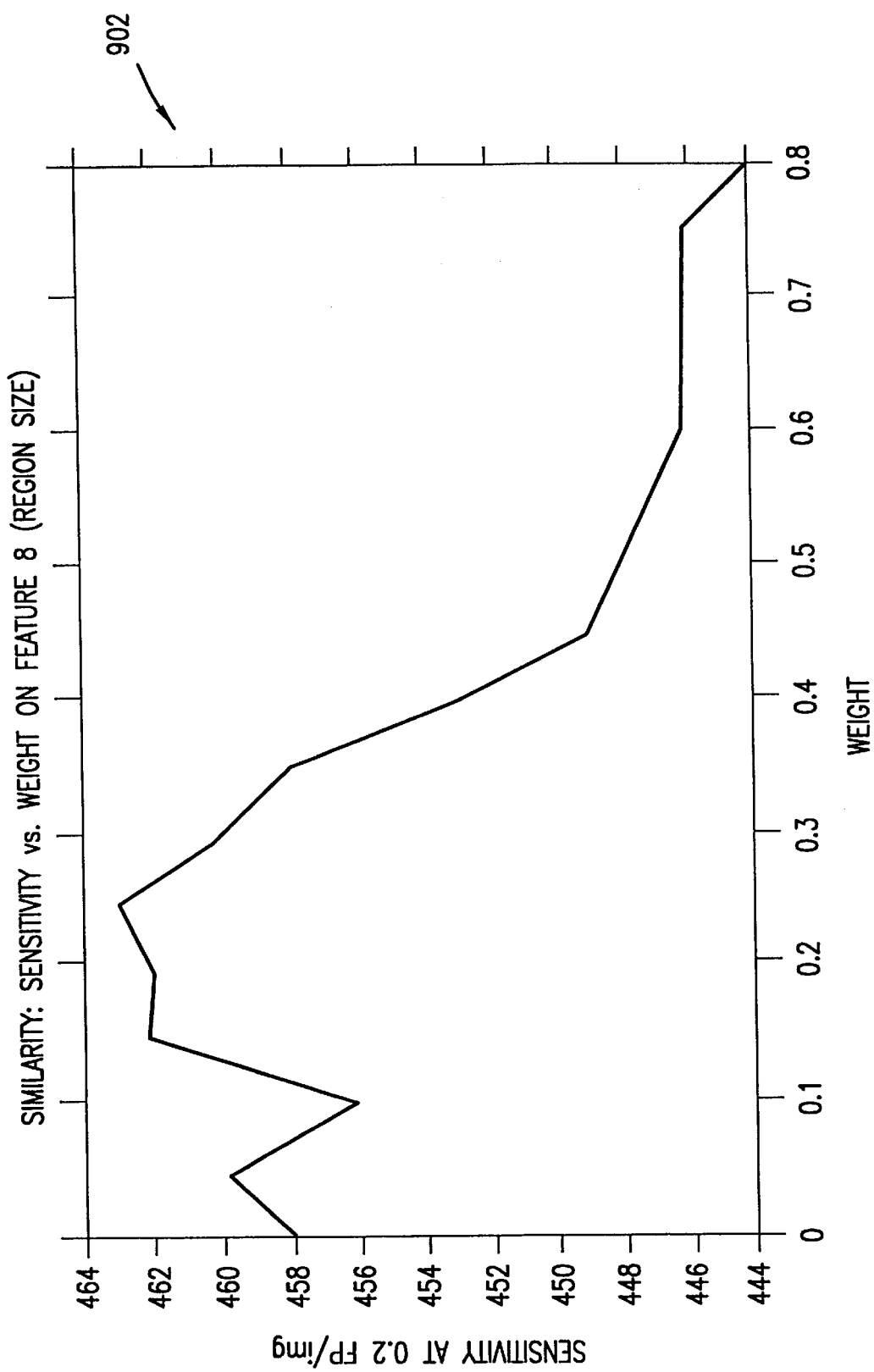
FIG. 9 shows an optimization curve used to generate an empirical determination of a weighting coefficient used in a computer-aided lesion detection device.

FIG. 9 shows an optimization curve 902 used to generate one empirical determination of one of the weights $a_0$, $a_1$, $a_2$, and $a_3$. In the example of FIG. 9 the weight $a_1$ supra, which is associated with region area or region size, is empirically derived, although the method disclosed herein may be applied by a person of skill in the art to a variety of different parameters in the system.

FIG. 9 is a plot 902 of system sensitivity at FP/Image=0.2 (the first quality measure disclosed above) against several trial values of the weight $a_1$ with other weights and system parameters fixed. To generate the curve of FIG. 9, the parameter $a_1$ is set, for example, to 0.5 with the other parameters being fixed at their pre-assumed values, for example, $a_0$ equal to 1.0. The sensitivity at 0.2 FP/Image is then determined as described supra and the value plotted on the system sensitivity plot 902 of FIG. 9 The weight $a_1$ is then changed to 0.1 and the process is repeated. The process is repeated for all values of $a_1$ up to a reasonable value that shows that an asymptotic or undesired behavior of sensitivity. The peak of the curve of plot 902 is then determined as the optimal value for $a_1$. It may be necessary to revisit the optimization of $a_1$ after optimizing the other weights, which may be done in an iterative process until convergence as appropriate. As shown in FIG. 9, a value of $a_1$=0.2 is found to be appropriate as it yields the greatest sensitivity of the overall system (at FP/Image=0.2).

Figure 10A:
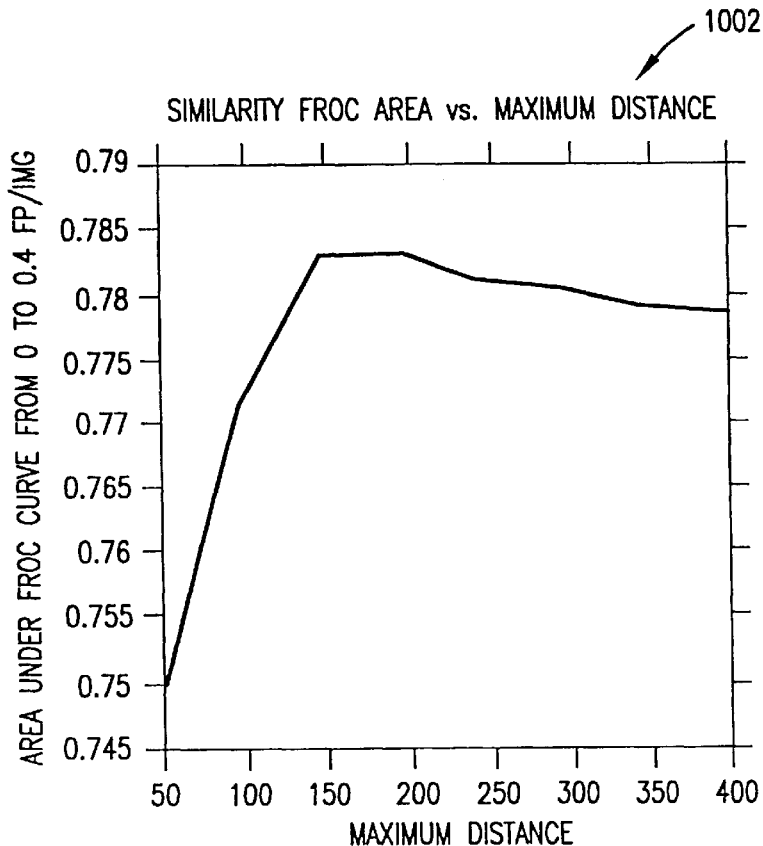
FIG. 10 shows clip distance optimization plots corresponding to a computer-aided lesion detection device.
Figure 10B:
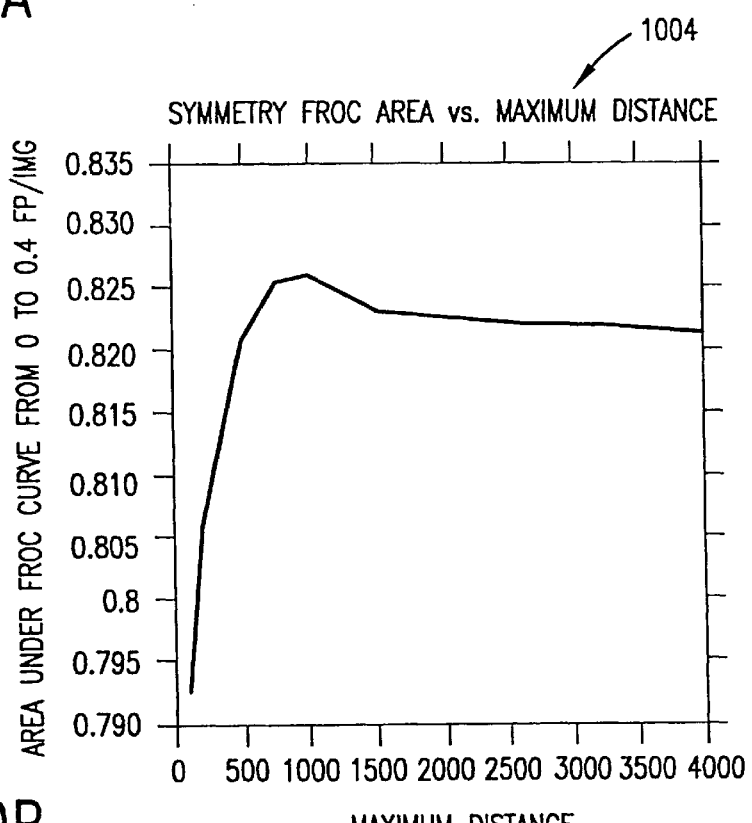

FIG. 10 shows clip distance optimization plots 1002 and 1004, each corresponding to the area under the FROC curve (the second quality metric described supra) versus certain maximum "clipped distances." In practice, there turns out to be a maximum distance within which to consider a "match" between views for potentially suspicious lesions, and between breasts for false regions (due to symmetric structures). These have been given the name "clip" values for similarity and symmetry. In particular, in a preferred embodiment, it is found that at step 608 of FIG. 6, for example, it is not necessary or desirable to compute a cost function for every single potentially suspicious lesion in the alternative mammogram view. Rather, it is desirable only to compute similarity metrics for potentially suspicious lesions that are within a maximum "clip" distance of each other, as determined by the difference between $R_{NIPPLE}$ for the respective lesions. These clip distances can be computed using the plots shown in FIG. 10.

Plot 1002 of FIG. 10 shows a clip distance optimization plot for the similarity metrics. In particular, plot 1002 is derived by first setting a certain maximum clip distance, e.g. 100 pixels. Thus, any two potentially suspicious lesions that are greater than 100 pixels away from each other are not considered in computing their respective similarity metrics. Using the technique described supra with respect to FIG. 8, the FROC curve is computed and the area thereunder from zero to 0.4 plotted. The maximum distance parameter is then increased to 150 and the process is repeated. The process is repeated for many values of maximum clip distance and the optimal value identified at the peak of plot 1002.

In the example of FIG. 10, it is found for example that the best maximum clip distance is 150 when considering similarity metrics. As shown in FIG. 10 at element 1004 similar techniques can be used to find maximum clip distance for symmetry comparisons as well. The plots of FIG. 10 are intuitively correct—if the maximum clip distance is extremely small, then similar features in alternate views will not be considered and will not be captured in the similarity metric and so the measure of quality is low. However if the maximum clip distance is very, very large, then there is no limitation at all on which potentially suspicious lesions are computed into the similarity metric and no value is added at all by using a maximum clip distance, as reflected by the asymptotic behavior of the curves. Finally, however, at an intermediate maximum distance, it is found that the quality measure increases because a proper radius of potentially suspicious lesions is considered.

Figure 11A:
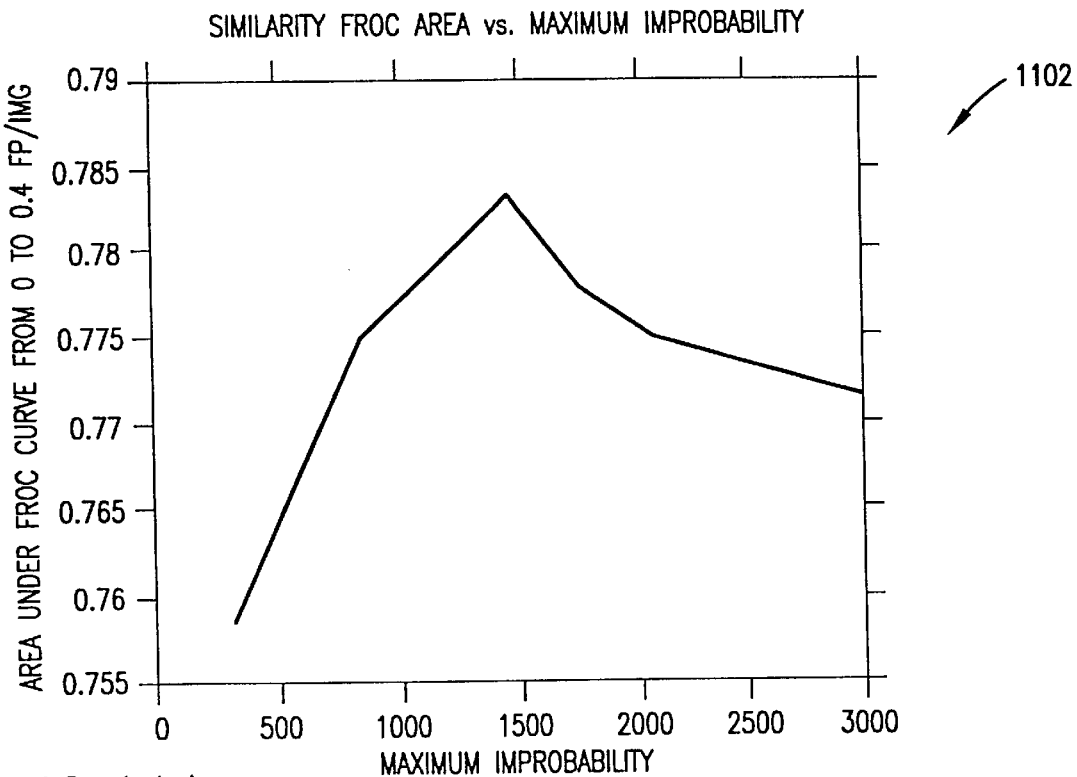
FIG. 11 shows optimization plots corresponding to a technique for determining a maximum improbability associated with suspicious lesions in alternate views.
Figure 11B:
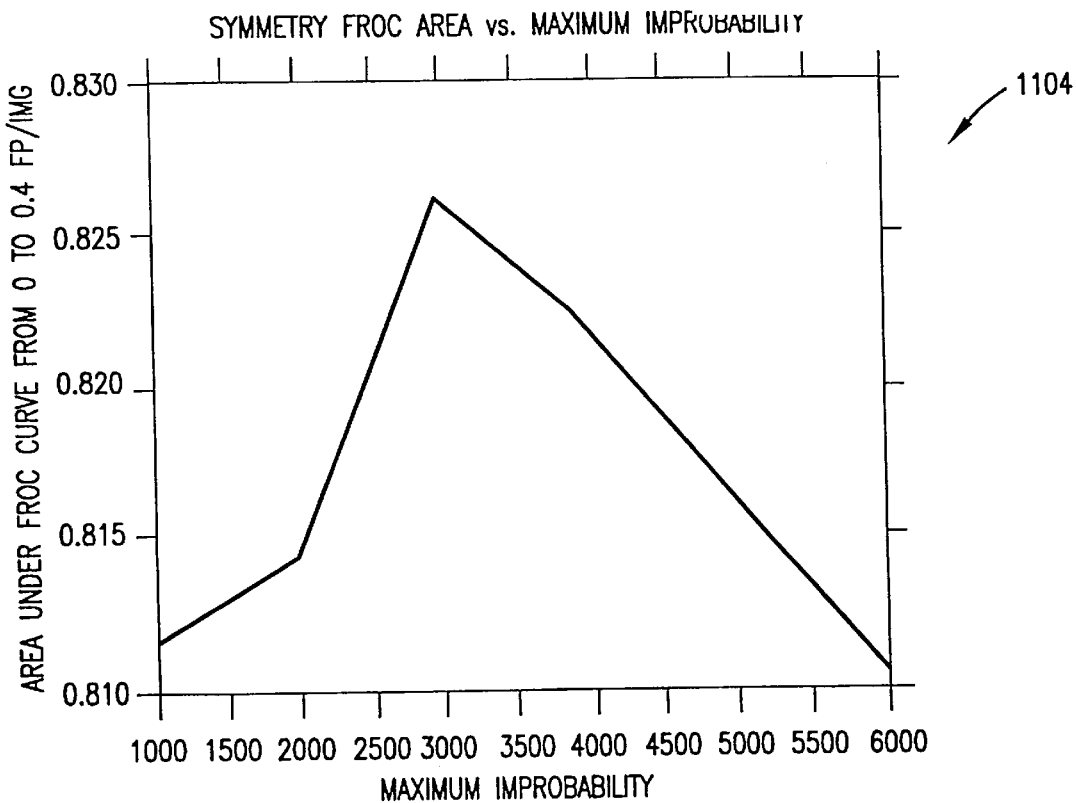

FIG. 11 shows optimization plots 1102 and 1104 corresponding to a technique for determining a maximum improbability associated with suspicious lesions in alternate views that may be used in a manner similar to the maximum clip distance in FIG. 10. In a preferred embodiment, a potentially suspicious lesion in an alternate view will not be considered in the computation of symmetry or similarity metrics unless it in itself has some certain minimum probability of being a potentially suspicious lesion. This step is taken in a preferred embodiment because inordinate weight might otherwise be given to very insignificant features that are nevertheless very close in feature-space distance to each other in the multiple views. Accordingly, a threshold probability of suspiciousness (as calculated from the single view lesion detection algorithm of steps 304–306, for example) should be set before all potentially suspicious lesions are identified and used in the computation of the similarity or symmetry metrics. Accordingly, FIG. 11 plots shows a change in threshold for probability versus the quality curve of the system on the vertical axis. The optimal value for maximum improbability is identified at the peaks of the respective curves.

While preferred embodiments of the invention have been described, these descriptions are merely illustrative and are not intended to limit the present invention. For example, although the embodiments of the invention described above were in the context of a system for computer aided diagnosis and detection of breast carcinoma in x-ray films, those skilled in the art will recognize that the disclosed methods and structures are readily adaptable for broader applications. For example, the invention is applicable to many other types of CAD systems for detection of other types of medical abnormalities.

What is claimed is:

1. A method for detecting suspicious lesions in a breast using information from a first digital mammogram view of the breast and a second digital mammogram view of the breast, comprising the steps of:

locating a first set of potentially suspicious lesions in said first digital mammogram view, each of said first set of potentially suspicious lesions having a single-view feature vector corresponding thereto;

locating a second set of potentially suspicious lesions in said second digital mammogram view;

computing a similarity metric between each of said first set of potentially suspicious lesions and each of said second set of potentially suspicious lesions; and classifying each of said first set of potentially suspicious lesions using information from the corresponding single-view feature vector and from the corresponding similarity metrics.

2. The method of claim 1, wherein said step of classifying each of said first set of potentially suspicious lesions is performed using a classification algorithm in which the single-view feature vector associated with that potentially suspicious lesion is processed along with the corresponding similarity metrics, and wherein a greater probability of suspiciousness is determined if that potentially suspicious lesion is highly similar to a potentially suspicious lesion in the second digital mammogram view.

3. The method of claim 2, each of said second set of potentially suspicious lesions also having a single-view feature vector, said single-view feature vectors associated with said first and second sets of potentially suspicious lesions comprising location information, wherein said step of computing a similarity metric comprises the step of comparing location information between each of said first set of potentially suspicious lesions and each of said second set of potentially suspicious lesions.

4. The method of claim 3, wherein said location information includes a nipple distance corresponding to a distance of the potentially suspicious lesion from the nipple of the breast in its respective digital mammogram view.

5. The method of claim 4, further comprising the step of locating the nipple of the breast in each digital mammogram view, said step of locating the nipple comprising the steps of:

segmenting that digital mammogram view for determining the position of the chest wall of the breast;

determining a most prominent direction of lines in the breast tissue relative to the chest wall for that digital mammogram view;

segmenting that digital mammogram view for determining the location of the skin line of the breast; and selecting the location of the nipple on that digital mammogram view as the furthest point along said skin line from said chest wall as measured along said most prominent direction of lines.

6. The method of claim 5, wherein said nipple distance is equal to the radial distance of the potentially suspicious lesion from the nipple in that digital mammogram view.

7. The method of claim 5, wherein said nipple distance is equal to the difference between (a) the distance of the nipple from the chest wall and (b) the distance of the potentially suspicious lesion from the chest wall.

8. The method of claim 5, wherein said single-view feature vector for each potentially suspicious lesion further comprises (1) an area metric related to the area of the potentially suspicious lesion, and (2) a contrast metric related to the contrast of the potentially suspicious lesion relative to the surrounding tissue area, and wherein said similarity metric is computed by computing a weighted distance in feature vector space between the potentially suspicious lesion in the first digital mammogram view and the potentially suspicious lesion in the second digital mammogram view.

9. The method of claim 8, wherein that potentially suspicious lesion is highly similar to the potentially suspicious lesion in the second digital mammogram view if said weighted distance in feature vector space has a low numerical value, wherein said weighted distance in feature vector space is a weighted Euclidean distance computed using the steps of:

determining a difference in nipple distance between the potentially suspicious lesion in the first digital mammogram view and the potentially suspicious lesion in the second digital mammogram view;

squaring said difference in nipple distance and weighting the result by a nipple distance weighting factor;

determining a difference in area metric between the potentially suspicious lesion in the first digital mammogram view and the potentially suspicious lesion in the second digital mammogram view;

squaring said difference in area metric and weighting the result by an area metric weighting factor; and computing said weighted Euclidean distance by computing the square root of the sum of said weighted squared differences.

10. The method of claim 9, wherein said nipple distance weighting factor is selected to be at least approximately five times greater than said area metric weighting factor.

11. The method of claim 10, said single-view feature vectors each further comprising a spiculation metric corresponding to the spiculatedness of the potentially suspicious lesion, wherein said weighted distance in feature vector space is further computed using the steps of:

determining a difference in spiculation metric between the potentially suspicious lesion in the first digital mammogram view and the potentially suspicious lesion in the second digital mammogram view;

squaring said difference in spiculation metric and weighting the result by a spiculation metric weighting factor;

determining a difference in contrast metric between the potentially suspicious lesion in the first digital mammogram view and the potentially suspicious lesion in the second digital mammogram view;

squaring said difference in contrast metric and weighting the result by a contrast metric weighting factor; and including said weighted squared spiculation and contrast metrics in said sum of said weighted squared differences.

12. A method for detecting suspicious lesions in a first breast using information from a first digital mammogram thereof and a second digital mammogram of an opposite breast, comprising the steps of:

locating a first set of potentially suspicious lesions in said first digital mammogram, each of said first set of potentially suspicious lesions having a single-view feature vector corresponding thereto;

locating a second set of potentially suspicious lesions in said second digital mammogram;

computing a symmetry metric between each of said first set of potentially suspicious lesions and each of said second set of potentially suspicious lesions; and classifying each of said first set of potentially suspicious lesions using information from the corresponding single-view feature vector and from the corresponding symmetry metrics relating that potentially suspicious lesion to potentially suspicious lesions in the opposite breast.

13. The method of claim 12, wherein said step of classifying each of said first set of potentially suspicious lesions is performed using a classification algorithm in which the single-view feature vector associated with that potentially suspicious lesion is processed along with the corresponding symmetry metrics relating that potentially suspicious lesion to potentially suspicious lesions in the opposite breast, and wherein a lesser probability of suspiciousness is determined if that potentially suspicious lesion is highly symmetric with a potentially suspicious lesion in the opposite breast.

14. The method of claim 13, each of said second set of potentially suspicious lesions also having a single-view feature vector, said single-view feature vectors associated with said first and second sets of potentially suspicious lesions comprising location information, wherein said step of computing a similarity metric comprises the step of comparing location information between each of said first set of potentially suspicious lesions and each of said second set of potentially suspicious lesions.

15. The method of claim 14, wherein said location information includes a nipple distance corresponding to a distance of the potentially suspicious lesion from the nipple of the breast in its respective digital mammogram.

16. The method of claim 15, further comprising the step of locating the nipple of the breast in each of said first and second digital mammograms, said step of locating the nipple in a respective digital mammogram comprising the steps of:

segmenting the digital mammogram for determining the position of the chest wall of the breast;

determining a most prominent direction of lines in the breast tissue relative to the chest wall for the digital mammogram;

segmenting the digital mammogram for determining the location of the skin line of the breast; and selecting the location of the nipple on the digital mammogram as the furthest point along said skin line from said chest wall as measured along said most prominent direction of lines.

17. The method of claim 16, wherein said nipple distance is equal to the radial distance of the potentially suspicious lesion from the nipple in the digital mammogram.

18. The method of claim 16, wherein said nipple distance is equal to the difference between (a) the distance of the nipple from the chest wall and (b) the distance of the potentially suspicious lesion from the chest wall.

19. The method of claim 15, wherein said single-view feature vector for each potentially suspicious lesion further comprises an area metric related to the area of the potentially suspicious lesion, and a contrast metric related to the contrast of the potentially suspicious lesion relative to the surrounding tissue area, and wherein said symmetry metric is computed by computing a weighted distance in feature vector space between the potentially suspicious lesion in the first digital mammogram and the potentially suspicious lesion in the second digital mammogram.

20. The method of claim 19, wherein that potentially suspicious lesion is highly symmetric with the potentially suspicious lesion in the second digital mammogram if said weighted distance in feature vector space has a low numerical value, wherein said weighted distance in feature vector space is a weighted Euclidean distance computed using the steps of:

determining a difference in nipple distance between the potentially suspicious lesion in the first digital mammogram and the potentially suspicious lesion in the second digital mammogram;

squaring said difference in nipple distance and weighting the result by a nipple distance weighting factor;

determining a difference in area metric between the potentially suspicious lesion in the first digital mammogram and the potentially suspicious lesion in the second digital mammogram;

squaring said difference in area metric and weighting the result by an area metric weighting factor; and computing said weighted Euclidean distance by computing the square root of the sum of said weighted squared differences.

21. The method of claim 20, wherein said nipple distance weighting factor is selected to be at least approximately five times greater than said area metric weighting factor.

22. The method of claim 21, said single-view feature vectors each further comprising a spiculation metric corresponding to the spiculatedness of the potentially suspicious lesion, wherein said weighted distance in feature vector space is further computed using the steps of:

determining a difference in spiculation metric between the potentially suspicious lesion in the first digital mammogram and the potentially suspicious lesion in the second digital mammogram;

squaring said difference in spiculation metric and weighting the result by a spiculation metric weighting factor;

determining a difference in contrast metric between the potentially suspicious lesion in the first digital mammogram and the potentially suspicious lesion in the second digital mammogram;

squaring said difference in contrast metric and weighting the result by a contrast metric weighting factor; and including said weighted squared spiculation and contrast metrics in said sum of said weighted squared differences.

23. A method for detecting suspicious lesions in a first breast using information from a first digital mammogram thereof taken from a first view, a second digital mammogram thereof taken from a second view different than the first view, and a third digital mammogram taken of an opposite breast, comprising the steps of:

locating a first set of potentially suspicious lesions in said first digital mammogram, each of said first set of potentially suspicious lesions having a single-view feature vector corresponding thereto;

locating a second set of potentially suspicious lesions in said second digital mammogram of the breast, each of said second set of potentially suspicious lesions having a single-view feature vector corresponding thereto;

locating a third set of potentially suspicious lesions in said third digital mammogram, each of said third set of potentially suspicious lesions having a single-view feature vector corresponding thereto;

computing a similarity metric between each of said first set of potentially suspicious lesions and each of said second set of potentially suspicious lesions;

computing a symmetry metric between each of said first set of potentially suspicious lesions and each of said third set of potentially suspicious lesions; and classifying each of said first set of potentially suspicious lesions using information from the (a) the corresponding single-view feature vector, (b) the corresponding similarity metrics relating that potentially suspicious lesion to potentially suspicious lesions in the different view of the same breast, and (c) the corresponding symmetry metrics relating that potentially suspicious lesion to potentially suspicious lesions in the opposite breast.

24. The method of claim 23, wherein said step of classifying each of said first set of potentially suspicious lesions is performed using a classification algorithm in which the single-view feature vector associated with that potentially suspicious lesion is processed along with the corresponding similarity and symmetry metrics, wherein a greater probability of suspiciousness is determined if that potentially suspicious lesion is highly similar to a potentially suspicious lesion in the second digital mammogram, and wherein a lesser probability of suspiciousness is determined if that potentially suspicious lesion is highly symmetric with a potentially suspicious lesion in the third digital mammogram.

25. The method of claim 24, said single-view feature vectors comprising location information, wherein said step of computing a similarity metric comprises the step of comparing location information between each of said first set of potentially suspicious lesions and each of said second set of potentially suspicious lesions, and wherein said step of computing a symmetry metric comprises the step of comparing location information between each of said first set of potentially suspicious lesions and each of said third set of potentially suspicious lesions.

26. The method of claim 25, wherein said location information includes a nipple distance corresponding to a distance of the potentially suspicious lesion from the nipple of the breast in its respective digital mammogram.

27. The method of claim 26, wherein said single-view feature vector for each potentially suspicious lesion further comprises an area metric related to the area of the potentially suspicious lesion, and a contrast metric related to the contrast of the potentially suspicious lesion relative to the surrounding tissue area, wherein said similarity metric is computed by computing a weighted distance in feature vector space between the potentially suspicious lesion in the first digital mammogram and the potentially suspicious lesion in the second digital mammogram, and wherein symmetry metric is computed by computing a weighted distance in feature vector space between the potentially suspicious lesion in the first digital mammogram and the potentially suspicious lesion in the third digital mammogram.

28. The method of claim 27, wherein that potentially suspicious lesion is highly similar to the potentially suspicious lesion in the second digital mammogram if said weighted distance in feature vector space has a low numerical value, wherein said weighted distance in feature vector space is a weighted Euclidean distance computed using the steps of:

determining a difference in nipple distance between the potentially suspicious lesion in the first digital mammogram and the potentially suspicious lesion in the second digital mammogram;

squaring said difference in nipple distance and weighting the result by a similarity nipple distance weighting factor;

determining a difference in area metric between the potentially suspicious lesion in the first digital mammogram and the potentially suspicious lesion in the second digital mammogram;

squaring said difference in area metric and weighting the result by an similarity area metric weighting factor; and computing said weighted Euclidean distance by computing the square root of the sum of said weighted squared differences.

29. The method of claim 28, wherein that potentially suspicious lesion is highly symmetric with the potentially suspicious lesion in the third digital mammogram if said weighted distance in feature vector space has a low numerical value, wherein said weighted distance in feature vector space is a weighted Euclidean distance computed using the steps of:

determining a difference in nipple distance between the potentially suspicious lesion in the first digital mammogram and the potentially suspicious lesion in the third digital mammogram;

squaring said difference in nipple distance and weighting the result by a symmetry nipple distance weighting factor;

determining a difference in area metric between the potentially suspicious lesion in the first digital mammogram and the potentially suspicious lesion in the third digital mammogram;

squaring said difference in area metric and weighting the result by an symmetry area metric weighting factor; and computing said weighted Euclidean distance by computing the square root of the sum of said weighted squared differences.

30. The method of claim 29, wherein said similarity nipple distance weighting factor is approximately equal to said symmetry nipple distance weighting factor, and wherein said similarity area metric weighting factor is approximately equal to aid symmetry area metric weighting factor.

31. The method of claim 30, wherein said similarity nipple distance weighting factor is at least approximately five times greater than said similarity area metric weighting factor.

32. A computer program product for directing a computer-aided lesion detection apparatus to detect suspicious lesions in a breast using information from a first digital mammogram view of the breast and a second digital mammogram view of the breast, comprising:

computer code for locating a first set of potentially suspicious lesions in said first digital mammogram view, each of said first set of potentially suspicious lesions having a single-view feature vector corresponding thereto;

computer code for locating a second set of potentially suspicious lesions in said second digital mammogram view;

computer code for computing a similarity metric between each of said first set of potentially suspicious lesions and each of said second set of potentially suspicious lesions; and computer code for classifying each of said first set of potentially suspicious lesions using information from the corresponding single-view feature vector and from the corresponding similarity metrics.

33. The computer program product of claim 32, wherein said computer code for classifying each of said first set of potentially suspicious lesions comprises computer code for performing a classification algorithm in which the single-view feature vector associated with that potentially suspicious lesion is processed along with the corresponding similarity metrics, and wherein a greater probability of suspiciousness is determined if that potentially suspicious lesion is highly similar to a potentially suspicious lesion in the second digital mammogram view.

34. A computer program product for directing a computer-aided lesion detection apparatus to detect suspicious lesions in a first breast using information from a first digital mammogram thereof and a second digital mammogram of an opposite breast, comprising:

computer code for locating a first set of potentially suspicious lesions in said first digital mammogram, each of said first set of potentially suspicious lesions having a single-view feature vector corresponding thereto;

computer code for locating a second set of potentially suspicious lesions in said second digital mammogram;

computer code for computing a symmetry metric between each of said first set of potentially suspicious lesions and each of said second set of potentially suspicious lesions; and computer code for classifying each of said first set of potentially suspicious lesions using information from the corresponding single-view feature vector and from the corresponding symmetry metrics relating that potentially suspicious lesion to potentially suspicious lesions in the opposite breast.

35. The computer program product claim 34, wherein said computer code for classifying each of said first set of potentially suspicious lesions comprises computer code for performing a classification algorithm in which the single-view feature vector is processed along with the corresponding symmetry metrics relating that potentially suspicious lesion to potentially suspicious lesions in the opposite breast, and wherein a lesser probability of suspiciousness is determined if that potentially suspicious lesion is highly symmetric with a potentially suspicious lesion in the opposite breast.

36. A computer program product directing a computer-aided lesion detection apparatus to detect suspicious lesions in a first breast using information from a first digital mammogram thereof taken from a first view, a second digital mammogram thereof taken from a second view different than the first view, and a third digital mammogram taken of an opposite breast, comprising:

computer code for locating a first set of potentially suspicious lesions in said first digital mammogram, each of said first set of potentially suspicious lesions having a single-view feature vector corresponding thereto;

computer code for locating a second set of potentially suspicious lesions in said second digital mammogram of the breast, each of said second set of potentially suspicious lesions having a single-view feature vector corresponding thereto;

computer code for locating a third set of potentially suspicious lesions in said third digital mammogram, each of said third set of potentially suspicious lesions having a single-view feature vector corresponding thereto;

computer code for computing a similarity metric between each of said first set of potentially suspicious lesions and each of said second set of potentially suspicious lesions;

computer code for computing a symmetry metric between each of said first set of potentially suspicious lesions and each of said third set of potentially suspicious lesions; and computer code for classifying each of said first set of potentially suspicious lesions using information from the (a) the corresponding single-view feature vector, (b) the corresponding similarity metrics relating that potentially suspicious lesion to potentially suspicious lesions in the different view of the same breast, and (c) the corresponding symmetry metrics relating that potentially suspicious lesion to potentially suspicious lesions in the opposite breast.

37. The computer program product of claim 36, wherein said computer code for classifying each of said first set of potentially suspicious lesions comprises computer code for performing a classification algorithm in which the single-view feature vector associated with that potentially suspicious lesion is processed along with the corresponding similarity and symmetry metrics, wherein a greater probability of suspiciousness is determined if that potentially suspicious lesion is highly similar to a potentially suspicious lesion in the second digital mammogram, and wherein a lesser probability of suspiciousness is determined if that potentially suspicious lesion is highly symmetric with a potentially suspicious lesion in the third digital mammogram.

38. A method for detecting suspicious lesions in a breast using information from a first digital mammogram thereof and a second digital mammogram thereof, comprising the steps of:

locating a first set of potentially suspicious lesions in said first digital mammogram, each of said first set of potentially suspicious lesions having a single-view feature vector corresponding thereto;

locating a second set of potentially suspicious lesions in said second digital mammogram;

computing a similarity metric between each of said first set of potentially suspicious lesions and each of said second set of potentially suspicious lesions; and classifying each of said first set of potentially suspicious lesions using information from the corresponding single-view feature vector and from the corresponding similarity metrics;

wherein said first digital mammogram and said second digital mammogram correspond to mammograms of the breast taken at substantially different times, whereby change in the breast over time that may indicate one or more cancerous conditions may be detected.

39. The method of claim 38, wherein said step of classifying each of said first set of potentially suspicious lesions is performed using a classification algorithm in which the single-view feature vector associated with that potentially suspicious lesion is processed along with the corresponding similarity metrics, and wherein a lesser probability of suspiciousness is determined if that potentially suspicious lesion is highly similar to one of said second set of potentially suspicious lesions in said second digital mammogram.

40. The method of claim 39, wherein said first digital mammogram and said second digital mammogram are least 6 months apart in time.

41. The method of claim 40, wherein said first digital mammogram is taken prior to said second digital mammogram.

42. A computer program product for directing a computer-aided lesion detection apparatus to detect suspicious lesions in a breast using information from a first digital mammogram thereof and a second digital mammogram thereof, comprising:
  computer code for locating a first set of potentially suspicious lesions in said first digital mammogram, each of said first set of potentially suspicious lesions having a single-view feature vector corresponding thereto;
  computer code for locating a second set of potentially suspicious lesions in said second digital mammogram;
  computer code for computing a similarity metric between each of said first set of potentially suspicious lesions and each of said second set of potentially suspicious lesions; and
  computer code for classifying each of said first set of potentially suspicious lesions using information from the corresponding single-view feature vector and from the corresponding similarity metrics;
  wherein said first digital mammogram and said second digital mammogram correspond to mammograms of the breast taken at substantially different times, whereby change in the breast over time that may indicate one or more cancerous conditions may be detected.

43. The computer program product of claim 42, wherein said computer code for classifying each of said first set of potentially suspicious lesions comprises computer code for performing a classification algorithm in which the single-view feature vector associated with that potentially suspicious lesion is processed along with the corresponding similarity metrics, and wherein a lesser probability of suspiciousness is determined if that potentially suspicious lesion is highly similar to one of said second set of potentially suspicious lesions in said second digital mammogram.

44. The computer program product of claim 42, wherein said first digital mammogram and said second digital mammogram are least 6 months apart in time.

45. The computer program product of claim 44, wherein said first digital mammogram is taken prior to said second digital mammogram.

46. A method for detecting suspicious lesions in a breast using information from a first digital mammogram thereof taken from a first view, a second digital mammogram thereof taken from a second view different than the first view, and a third digital mammogram thereof taken at a time prior to the time at which the first digital mammogram was taken, comprising the steps of:
  locating potentially suspicious lesions in each of said first, second, and third digital mammograms to produce a first, second, and third set of potentially suspicious lesions, respectively, each of said potentially suspicious lesions having a single-view feature vector corresponding thereto;
  computing a similarity metric between each of said first set of potentially suspicious lesions and each of said second set of potentially suspicious lesions;
  computing a similarity metric between each of said first set of potentially suspicious lesions and each of said third set of potentially suspicious lesions; and
  classifying each of said first set of potentially suspicious lesions using information from the (a) the corresponding single-view feature vector, (b) the corresponding similarity metrics relating that potentially suspicious lesion to potentially suspicious lesions in the second digital mammogram, and (c) the corresponding similarity metrics relating that potentially suspicious lesion to potentially suspicious lesions in the third digital mammogram;
  wherein said step of classifying each of said first set of potentially suspicious lesions is performed using a classification algorithm in which the single-view feature vector associated with that potentially suspicious lesion is processed along with the corresponding similarity metrics, wherein a greater probability of suspiciousness is determined if that potentially suspicious lesion is highly similar to a potentially suspicious lesion in the second digital mammogram view, and wherein a lesser probability of suspiciousness is determined if that potentially suspicious lesion is highly similar to a potentially suspicious lesion in the third digital mammogram view.

47. A method for detecting suspicious lesions in a breast using information from a first digital mammogram thereof taken from a first view, a second digital mammogram thereof taken at a time prior to the time at which the first digital mammogram was taken, and a third digital mammogram of the opposing breast, comprising the steps of:
  locating potentially suspicious lesions in each of said first, second, and third digital mammograms to produce a first, second, and third set of potentially suspicious lesions, respectively, each of said potentially suspicious lesions having a single-view feature vector corresponding thereto;
  computing a similarity metric between each of said first set of potentially suspicious lesions and each of said second set of potentially suspicious lesions;
  computing a symmetry metric between each of said first set of potentially suspicious lesions and each of said third set of potentially suspicious lesions; and
  classifying each of said first set of potentially suspicious lesions using information from the (a) the corresponding single-view feature vector, (b) the corresponding similarity metrics relating that potentially suspicious lesion to potentially suspicious lesions in the second digital mammogram, and (c) the corresponding symmetry metrics relating that potentially suspicious lesion to potentially suspicious lesions in the third digital mammogram;
  wherein said step of classifying each of said first set of potentially suspicious lesions is performed using a classification algorithm in which the single-view feature vector associated with that potentially suspicious lesion is processed along with the corresponding symmetry and similarity metrics, wherein a lesser probability of suspiciousness is determined if that potentially suspicious lesion is highly similar to a potentially suspicious lesion in the second digital mammogram view, and wherein a lesser probability of suspiciousness is determined if that potentially suspicious lesion is highly symmetric with a potentially suspicious lesion in the third digital mammogram view.

* * * * *